US006271211B1

(12) United States Patent
Christ et al.

(10) Patent No.: US 6,271,211 B1
(45) Date of Patent: Aug. 7, 2001

(54) GENE THERAPY FOR REGULATING PENILE SMOOTH MUSCLE TONE

(75) Inventors: George J. Christ, Smithtown; Arnold Melman, Ardsley, both of NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/532,138

(22) Filed: Mar. 21, 2000

Related U.S. Application Data

(63) Continuation-in-part of application No. 08/799,144, filed on Feb. 13, 1997, and a continuation-in-part of application No. 09/135,849, filed on Aug. 18, 1998.

(51) Int. Cl.[7] ............................ A01N 43/04; A61K 31/70; C12N 15/00; C12N 15/09; C12N 15/63

(52) U.S. Cl. ...................... 514/44; 435/320.1; 435/325; 435/455; 530/350; 536/23.1; 536/23.5

(58) Field of Search ................... 514/44; 530/350; 536/23.1, 23.5; 435/328.1, 325, 455

(56) References Cited

U.S. PATENT DOCUMENTS

| 5,214,030 | 5/1993 | Stief ........................................ 514/12 |
| 5,219,748 | 6/1993 | Yoshitaka et al. ..................... 435/194 |
| 5,324,651 | 6/1994 | Ono et al. ............................. 435/194 |
| 5,594,032 | 1/1997 | Gonzalez-Cadavid et al. ...... 514/645 |
| 6,150,338 | 11/2000 | Geliebter et al. ...................... 514/44 |

FOREIGN PATENT DOCUMENTS

| WO 98/33529 | 8/1998 | (WO) . |
| WO 98/36055 | 8/1998 | (WO) . |
| WO 00/10604 | 3/2000 | (WO) . |

OTHER PUBLICATIONS

Christ, G.J., A new frontier: gene therapy for erectile dysfunction. In Erectile Dysfunction: issues in current pharmacotherapy (London: Martin Dunitz Ltd., 1998), chap.13, 209–30.
Christ, G.J., The control of corporal smooth muscle tone, the coordination of penile erection, and the etiology of erectile dysfunction: the devil is in the details. J. Sex Edu. & Ther., 23;187–93, 1998.
Christ, G.J., The "syncytial tissue triad": a model for understanding how gap junctions participate in the local control of penile erection. World J. Urol., 15:36–44, 1997.
Christ, G.J., The penis as a vascular organ. The importance of corporal smooth muscle tone in the control of erection. Urol. Clin. North Am., 22(4):727–45, Nov. 1995.
Christ and Brink, Gap junctions in isolated rat aorta: evidence for contractile responses that exhibit a differential dependence on intercellular communication. Braz. J. Med. Biol. Res., 33(4):423–29, 2000.

Christ and Melman, The application of gene therapy to the treatment of erectile dysfunction. Int. J. Impot. Res., 10:111–12, 1998.
Christ and Melman, Molecular studies of human corporal smooth muscle: implications for the understanding, diagnosis, and treatment of erectile dysfunction. Mol. Urol., 1(1):45–54, Nov. 1997.
Christ et al., Ion channels and gap junctions: their role in erectile physiology, dysfunction, and future therapy. Mol. Urol., 3:61–73, 1999.
Christ et al., Intracorporal injection of hSlo cDNA in rats produces physiologically relevant alterations in penile function. Am. J. Physiol., 275:H600–H608, 1998.
Christ et al., Integrative erectile biology: the role of signal transduction and cell–to–cell communication in coordinating corporal smooth muscle tone and penile erection. Int. J. Impot. Res., 9:69–84, 1997.
Christ et al., Characterization of K currents in cultured human corporal smooth muscle cells. J. Androl., 14(5):319–28, Sep./Oct. 1993.
Christ et al., The role of gap junctions and ion channels in the modulation of electrical and chemical signals in human corpus cavernosum smooth muscle. Int. J. Impot. Res., 5:77–96. 1993.
Crystal, R.G., Transfer of genes to humans: early lessons and obstacles to success. Science, 270:404–10, 1995.
Deonarain, M.P., Ligand–targeted receptor–mediated vectors for gene delivery. Exp. Opin. Ther. Patents, 8(1):53–69, 1998.
Eck and Wilson, Gene–based therapy. In The Pharmacological Basis of Therapeutics, 9th ed. (New York: McGraw–Hill, 1995), chap. 5, 77–101.
Fan et al., An analysis of the max–K+ (KCa) channel in cultured human corporal smooth muscle cells. J. Urol., 153:818–25, Mar. 1995.

(List continued on next page.)

*Primary Examiner*—Karen M. Hauda
*Assistant Examiner*—Peter Paras, Jr.
(74) *Attorney, Agent, or Firm*—Amster, Rothstein & Ebenstein

(57) ABSTRACT

The present invention is directed towards a method of regulating smooth muscle tone, comprising the introduction, into smooth muscle cells of a subject, of a DNA sequence encoding a protein involved in the regulation of smooth muscle tone, and expression of the DNA sequence in a sufficient number of smooth muscle cells of the subject to regulate smooth muscle tone in the subject. Specifically, the invention provides methods of gene therapy for treating erectile dysfunction, bladder dysfunction, and other smooth muscle disorders. The present invention also provides recombinant viral and non-viral vectors comprising DNA encoding a protein involved in the regulation of smooth muscle tone. Further provided by the present invention is a smooth muscle cell which expresses a gene encoding a protein involved in the regulation of smooth muscle tone.

2 Claims, 23 Drawing Sheets

OTHER PUBLICATIONS

Gopalakrishnan et al., Pharmacology of human sulphonylurea receptor SUR1 and inward rectifier K+ channel Kir6.2 combination expressed in HEK-293 cells. Brit. J. Pharmacol., 129:1323-32, 2000.

Lee et al., Characterization of ATP-sensitive potassium channels in human corporal smooth muscle cells. Int. J. Impot. Res., 11:179-88, 1999.

Lee et al., Prostaglandin E1 activates the large-conductance KCa channel in human corporal smooth muscle cells. Int. J. Impot. Res., 11:189-99, 1999.

Lerner et al., A review of erectile dysfunction: new insights and more questions. J. Urol., 149:1246-55, May 1993.

McCobb et al., A human calcium-activated potassium channel gene expressed in vascular smooth muscle. Am. J. Physiol., 269(3):H767-H777, Sep. 1995.

Melman and Christ, The hemodynamics of erection and the pharmacotherapy of erectile dysfunction. In Cardiovascular Pharmacotherapeutics, J. Hefta and P. Touboul, eds. (New York: McGraw-Hill, 1997), chap. 56, 1221-29.

Miller and Vile, Targeted vectors for gene therapy. FASEB J., 9:190-99, Feb. 1995.

Nabel et al., Site-specific gene expression in vivo by direct gene transfer into the arterial wall. Science, 249:1285-88, Sep. 1990.

Rehman et al., Experimental hyperprolactinemia in a rat model: alteration in centrally mediated neuroerectile mechanisms. Int. J. Impot. Res., 12:23-32, 2000.

Rehman et al., Diminished neurogenic but not pharmacological erections in the 2- to 3-month experimentally diabetic F-344 rat. Am. J. Physiol., 272:H1960-H1971, 1997.

Serels et al., Molecular studies of human connexin 43 (Cx43) expression in isolated corporal tissue strips and cultured corporal smooth muscle cells. Int. J. Impot. Res., 10:135-43, 1998.

Verma and Somia, Gene therapy—promises, problems and prospects. Nature, 389:239-42, Sep. 1997.

Wang et al., Comparative studies of the maxi-K (KCa) channel in freshly isolated myocytes of human and rat corpora. Int. J. Impot. Res., 12:9-18, 2000.

Wegner et al., Nitric oxide donor, linsidomine chlorhydrate (SIN-1), in the diagnosis and treatment of erectile dysfunction: critical appraisal and review of the literature. Int. Urol. & Nephrol, 27(5):621-28, 1995.

Crystal et al, 1995, Science, 270: 404-410.*

Deonarain, 1998, Exp. Opin. Ther. Patents, 8(1): 53-69.*

Eck and Wilson, 1995, The Pharmacological Basis of Therapeutics, 9th edition, McGraw-Hill, pp. 77-101.*

Miller et al, 1995, FASEB J., 9: 190-199.*

Verma et al, 1997, Nature, 389: 239-242.*

Gapalakrishnan et al, 2000, Brit. J. Pharm., 129: 1323-1332.*

* cited by examiner

GENE THERAPY FOR REGULATING PENILE SMOOTH MUSCLE TONE

CROSS-REFERENCE TO RELATED APPLICATIONS

This is a continuation-in-part of copending U.S. application Ser. No. 08/799,144, filed Feb. 13, 1997, and a continuation-in-part of copending U.S. application Ser. No. 09/135,849, filed Aug. 18, 1998, both of which are hereby incorporated by reference in their entireties.

BACKGROUND OF THE INVENTION

There are many physiological dysfunctions or disorders which are caused by the deregulation of smooth muscle tone. Included among these dysfunctions and disorders are: asthma; benign hyperplasia of the prostate gland (BHP); coronary artery disease (infused during angiography); erectile dysfunction; genitourinary dysfunctions of the bladder, endopelvic fascia, prostate gland, ureter, urethra, urinary tract, and vas deferens; irritable bowel syndrome; migraine headaches; premature labor; Raynaud's syndrome; and thromboangitis obliterans.

Erectile dysfunction is a common illness that is estimated to affect 10 to 30 million men in the United States (Feldman, et al., *Journal of Clinical Epidemiology*, 47(5):457–67, 1994; and Anonymous, *International Journal of Impotence Research*, 5(4):181–284, 1993). Among the primary disease-related causes of erectile dysfunction are aging, atherosclerosis, chronic renal disease, diabetes, hypertension and antihypertensive medication, pelvic surgery and radiation therapy, and psychological anxiety (Feldman, et al., *Journal of Clinical Epidemiology*, 47(5):457–67, 1994). Direct cures for the vascular ravages of these manifold and multifaceted disease states are unlikely to occur in the near future.

The last decade has witnessed the development of several treatment modalities to directly restore diminished erectile capacity. However, all currently-available therapies are either nonspecific (e.g., hormonal therapy), of limited overall success (e.g., vacuum erection devices), invasive (e.g., intracorporal injection therapy), or non-reversible and expensive (e.g., penile prosthetic implant surgery). Despite these therapeutic limitations, the FDA's approval of CAVERJECT® (Jul. 6, 1995) for intravacernous treatment of erectile dysfunction, of MUSE® (Nov. 19, 1996) for intra-urethral drug administration in the treatment of erectile dysfunction, and of Viagra® (Mar. 27, 1998) as an oral therapeutic agent for treatment of erectile dysfunction, represent major steps forward. In essence, these acts of the Federal Government have resulted in the formal recognition of the medical nature of the problem of erectile dysfunction, and, furthermore, have legitimized its clinical treatment.

Recent changes in contemporary cultural patterns in the United States have allowed for a free and more open public discussion of sex and sexual dysfunction. This cultural trend has highlighted the magnitude of the problem of erectile dysfunction, and has simultaneously emphasized the need for improved clinical treatment of the condition. The recent deluge of advertising and media activity related to the discussion and treatment of erectile dysfunction has made men, and their sexual partners, more aware that erectile dysfunction is a common problem, with legitimate (i.e., federally-approved) clinical treatments available. This combination of events will continue to prompt even larger numbers of men, over the next decade, to seek treatment for impotence.

The magnitude of the problem of erectile dysfunction, and the desire for more effective therapies, are highlighted by the nearly 2 million prescriptions written for VIAGRA since April 1998. Thus, there is now a well-recognized need for a better understanding of the impact of age and disease on human erection; this understanding can be gained, in part, by studying the function of corporal and arterial smooth muscle at the whole-tissue, cellular, and, most recently, subcellular levels. Also needed is a research strategy that will permit the direct translation of the results of laboratory work to the clinical environment, ensuring that new treatments for organic erectile dysfunction will be more cost effective, of greater efficacy, and of longer duration, and will be accompanied by fewer side effects.

Studies have documented that altered corporal smooth muscle tone, resulting in either heightened contractility or impaired relaxation, is a proximal cause of erectile dysfunction in a large proportion of impotent men. These studies have further indicated that complete relaxation of corporal smooth muscle is both a necessary and sufficient condition to restoring erectile potency, unless severe arterial disease or congenital structural abnormalities exist; the latter is true in only a minority of patients. The efficacy of recently-approved therapies for treating erectile dysfunction, which involve agents for directly or indirectly bringing about smooth-muscle relaxation - including $GE_1$ (CAVERJECT®, EDEX®, and MUSE®) and Sildenafil (VIAGRA®) - verifies the validity of this supposition.

As described above, the critical role in erectile function played by corporal smooth muscle cells makes them an excellent target for molecular intervention in the treatment of erectile dysfunction. Previous efforts have focused on techniques for gene transfer into vascular smooth muscle cells as a basis for the potential therapy of several cardio-vascular diseases. Among these are atherosclerosis, vasculitis, and restenosis after balloon angioplasty. These initial studies have provided important information on the efficiency and persistence of gene-transfer methods in smooth muscle cells (Finkel, et al., *FASEB Journal*, 9:843–51, 1995).

Because erectile dysfunction is largely caused by altered smooth muscle tone, a method of gene therapy which targets the genes involved in the alteration of smooth muscle tone is extremely desirable. Of critical importance with respect to all in vivo gene-therapy approaches are the percentage of target cells that must be affected in order to see a physiologically—relevant therapeutic effect, and the relative efficiency of affecting only the desired cell type(s). Accordingly, there is a need for a method of gene therapy wherein only a small number of cells need to be genetically modified in order to effect global changes in tissue function. A successful method of gene therapy for alleviating erectile dysfunction is in great demand, as it would be a preferred alternative to currently-used methods.

Abnormal bladder function is another common problem which significantly affects the quality of life of millions of men and women in the United States. Many common diseases (e.g., BHP, diabetes mellitus, multiple sclerosis, and stroke) alter normal bladder function. Significant untoward changes in bladder function are also a normal result of advancing age.

There are two principal clinical manifestations of altered bladder physiology: the atonic bladder and the hyperreflexic bladder. The atonic bladder has diminished capacity to empty its urine contents because of ineffective contractility of the detrusor smooth muscle (the outer smooth muscle of the bladder wall). In the atonic state, diminished smooth muscle contractility is implicated in the etiology of bladder dysfunction. Thus, it is not surprising that pharmacological modulation of smooth muscle tone is insufficient to correct the underlying problem. In fact, the prevailing method for treating this condition uses clean intermittent catheterization; this is a successful means of preventing chronic urinary tract infection, pyelonephritis, and eventual renal failure. As such, treatment of the atonic bladder ameliorates the symptoms of disease, but does not correct the underlying cause.

Conversely, the hyperreflexic, or uninhibited, bladder contracts spontaneously; this may result in urge incontinence, where the individual is unable to control the passage of urine. The hyperreflexic bladder is a more difficult problem to treat. Medications that have been used to treat this condition are usually only partially effective, and have severe side effects that limit the patient's use and enthusiasm. The currently-accepted treatment options (e.g., oxybutynin and tolteradine) are largely nonspecific, and most frequently involve blockade of the muscarinic-receptor pathways and/or the calcium channels on the bladder myocytes. Given the central importance of these two pathways in the cellular functioning of many organ systems in the body, such therapeutic strategies are not only crude methods for modulating bladder smooth muscle tone; rather, because of their very mechanism(s) of action, they are also virtually guaranteed to have significant and undesirable systemic effects. Accordingly, there is a great need for improved treatment options for bladder dysfunction.

With life expectancy still increasing, the incidence of bladder dysfunction will only continue to rise. Based on the extensive evidence already accumulated in another urogenital smooth-muscle-cell type, namely, the corporal smooth muscle cell, the inventors strongly believe that specific end-organ modulation of bladder myocyte tone is the best strategy for correcting bladder dysfunction.

There are some physiologically-relevant parallels between penile physiology and bladder physiology which bear comparison. For example, the tone of the detrusor smooth muscle plays a role in the etiology of bladder dysfunction that is similar to the well-characterized role of corporal smooth muscle tone in erectile dysfunction. In particular, the hyperreflexic bladder is characterized by heightened contractility, while the atonic bladder is characterized by impaired contractility. Pharmacological therapy for treating ladder hyperreflexia typically involves frequent intravesical instillations, a treatment that patients often find inconvenient or otherwise undesirable. In short, frequent intravesical instillations to restore bladder myocyte function are undesirable, and systemic medications still lack tolerable specificity. Nevertheless, the critical role in bladder function played by the detrusor smooth muscle cells, and their accessibility across the urothelium through intravesical instillations, make them excellent targets for molecular intervention in the treatment of bladder dysfunction.

Because erectile dysfunction and bladder dysfunction are largely caused by altered smooth muscle tone, a method of gene therapy which targets the genes involved in the regulation of smooth muscle tone is extremely desirable, for it would provide a new means of alleviating bladder dysfunction and erectile dysfunction. Similarly, a method of gene therapy which targets the genes involved in the regulation of smooth muscle tone would be extremely useful as a means of alleviating other smooth muscle dysfunctions, including, but not limited to, asthma; benign hyperplasia of the prostate gland (BHP); coronary artery disease (infused during angiography); genitourinary dysfunctions of the endopelvic fascia, prostate gland, ureter, urethra, urinary tract, and vas deferens; irritable bowel syndrome; migraine headaches; premature labor; Raynaud's syndrome; and thromboangitis obliterans.

Current methods of gene therapy use retroviral-based or adenoviral-based recombinant vectors to infect a target cell. Such vectors, however, present certain problems which have not been resolved to date. For instance, retroviral- and adenoviral-based vectors most often elicit an immune response from the subject being treated. Because of this immune response, the vectors cannot be maintained in the cells, and the DNA is not transcribed from the vectors. Furthermore, in order for a global change to occur in the cells surrounding an infected cell, each cell must be infected individually by the recombinant vector. Thus, this method of gene therapy relies upon the efficiency of transfection. Other side effects resulting from the use of retroviral- or adenoviral-based vectors include insertional mutagenesis. Accordingly, there is clearly a need for a method of gene therapy which does not use retroviral- or adenoviral-based vectors, which does not rely upon the efficiency of transfection of a vector, but which is still able to effect global changes in a tissue by modification of only a fraction of the cells.

SUMMARY OF THE INVENTION

The present invention is directed towards a method of gene therapy for regulating smooth muscle tone in a subject. The method comprises introducing into the smooth muscle cells of the subject a DNA sequence encoding a protein involved in the regulation of smooth muscle tone, such that the DNA sequence is expressed in a sufficient number of smooth muscle cells of the subject to alter smooth muscle tone in the subject.

The present invention further provides methods of gene therapy, wherein the DNA sequence which encodes a protein involved in the regulation of smooth muscle tone encodes a protein which modulates contraction of smooth muscle. Such a protein will enhance smooth muscle contraction, thereby restoring smooth muscle tone.

The present invention also provides methods of gene therapy, wherein the DNA sequence which encodes a protein involved in the regulation of smooth muscle tone encodes a protein which modulates relaxation of smooth muscle. Such a protein will enhance smooth-muscle relaxation, thereby restoring smooth muscle tone.

In a specific embodiment of the invention, the methods of gene therapy described herein are used to alleviate erectile dysfunction. In another embodiment of the invention, the described methods of gene therapy are used to alleviate bladder dysfunction. In other embodiments of the invention, the methods of gene therapy are used to alleviate dysfunctions of the blood vessel walls, bowel, bronchi of the lungs, endopelvic fascia, prostate gland, ureter, urethra, urinary tract, uterus, and vas deferens. Specifically, the methods of gene therapy are used to treat smooth muscle dysfunctions, including, but not limited to, asthma; benign hyperplasia of the prostate gland (BHP); coronary artery disease (infused during angiography); genitourinary dysfunctions of the endopelvic fascia, prostate gland, ureter, urethra, urinary tract, and vas deferens; irritable bowel syndrome; migraine headaches; premature labor; Raynaud's syndrome; and thromboangitis obliterans. When used to treat asthma, the present method of gene therapy may be delivered to a subject through an aerosol carrier.

The present invention further provides viral and non-viral recombinant vectors, comprising a nucleic-acid sequence encoding a protein involved in the regulation of smooth muscle tone.

The present invention additionally provides for a smooth muscle cell that expresses a DNA sequence encoding a protein involved in the regulation of smooth muscle tone.

Additional objects of the invention will be apparent from the description which follows.

BRIEF DESCRIPTION OF THE FIGURES

FIG. 1 illustrates how selective blockade of the maxi-K channel alters the nitroglycerine-induced relaxation response in isolated human corporal tissue strips. A modification of a previously-published kinetic protocol as used (Christ, et al., *American Journal of Physiology*, 263:H15–H19, 1992) to derive two parameters: $\tau_{1/2}$, the time elapsed from addition of nitroglycerine (NTG) to achievement of 50% of the steady-state relaxation response; and RSS, the steady-state magnitude of the nitroglycerine-induced relaxation response. Note that preincubation of isolated corporal tissue strips resulted in a significant reduction in the magnitude of the NTG-induced relaxation response (100 nM). pe=phenylephrine.

FIG. 2 sets forth an illustration of K-channel function and the control of corporal smooth muscle tone. (+) denotes a positive or stimulatory effect; (–) denotes a negative or inhibitory effect; and ? denotes an unknown action. DAG=diacylglycerol; ET–1=endothelin-1; $IP_3$=inositoltrisphosphate; L-type $Ca^{2+}$=L-type, voltage-dependent calcium channel; NO=nitric oxide; NTG=the nitrate donor, nitroglycerine; PE=phenylephrine; $PGE_1$=prostaglandin $E_1$; $PIP_2$=phosphatidylinositol bisphosphate FIG. 3 depicts the surgical preparation and placement of pressure-monitoring cannulas.

FIG. 4 sets forth the results of experiments which determined the fractional change in intracorporal pressure (ICP) in response to neurostimulation.

FIG. 5 is a diagram which indicates the major mechanisms regulating corporal smooth muscle tone. Shown are two corporal smooth muscle cells, interconnected at their lateral border by a gap-junction plaque. Also shown are voltage-dependent calcium ($Ca^{2+}$) channels, and potassium ($K^+$) channels. The left cell depicts the series of intracellular events linked to corporal smooth-muscle contraction (an elevation in intracellular $Ca^{2+}$ levels), while the right depicts the series of intracellular events linked to corporal smooth-muscle relaxation (a decrease in intracellular $Ca^{2+}$ levels). (+) means a stimulatory, positive, or increasing effect, and (–) means an inhibitory or negative effect.

FIG. 6 is a photograph of the results of a gene transfer experiment in the rat bladder. The bladder on the left received intravesical instillation of 65 μg of LacZ cDNA. The bladder on the right is the control bladder.

FIGS. 7(A–B): FIG. 7A shows intact corpus cavernosum from rat that was injected with pCMVβ plasmid containing the LacZ gene. Note the expression of β-galactosidase activity, with concomitant formation of the chromogenic substrate and characteristic blue color. This photograph was taken 60 days after the original injection. The robust blue staining is largely confined to the injected corpora, particularly near the injection site (arrow). FIG. 7B shows corpus cavernosum from an age-matched control rat that was not injected with plasmid. Note the complete absence of any blue staining in the corporal tissue (arrow) of this uninjected control animal.

FIG. 8 depicts a representative time course of changes in mean arterial blood pressure (open symbols) and intracorporal pressure (closed symbols) during neurostimulation (2 mA) for an age-matched control animal, a maxi-K-transfected animal, and a young control animal. As described in the Experimental Details Section, the maxi-K-transfected animal was subjected to a single intracavernous injection of the pcDNA/hSlo naked DNA three months prior to this experiment, while the age-matched control animal received the pcDNA vector only, without the hSlo cDNA. Note the dramatic difference in mean amplitude of the intracorporal pressure responses of the maxi-K-transfected animal and the age-matched control animal, despite the similarity in their mean arterial blood pressures.

FIG. 9 shows a summary of all in vivo data for intracorporal pressure measurements in response to electrical stimulation of the cavernous nerve in age-matched control animals, maxi-K-transfected animals, and young control animals. Shown are the mean values (±S.E.M.) of the mean amplitudes of the intracorporal pressure responses recorded in all animals in each treatment category, at every level of current stimulation examined in these studies. Note that, for the purposes of this illustrative comparison, all of the maxi-K-transfected and age-matched control animals were combined as a single population. N refers to the total number of animals in each treatment category.

FIGS. 10(A–C)

FIGS. 11(A–C)

FIG. 12 sets forth the results of a Northern blot showing incorporation of recombinant human $K_{Ca}$ into rat corporal smooth muscle. Total RNA (20 μg each) was obtained from recombinant human pcDNA/$K_{Ca}$-transfected rat corporal tissue, pcDNA-transfected control rat corporal tissue, and uninjected control rat corporal tissue, and was hybridized with a biotin-labeled hSlo cDNA full-length probe for the human sequence. As shown, this full-length hSlo cDNA detected a band in the pcDNA/$K_{Ca}$-transfected rat tissue, but not in pcDNA-transfected, nor in uninjected control, rat tissue. The size of the recombinant human $K_{Ca}$ mRNA is ~4.0 Kb. Note that the sequence homology of the rat and human $K_{Ca}$ channels is approximately 90%, which corresponds to about 350 base-pair differences. Under the high stringency conditions used in this assay, therefore, it would be expected that the full-length probe would recognize only the recombinant $K_{Ca}$, and not the endogenous $K_{Ca}$ sequence.

FIG. 13 presents a schematic diagram depicting the proposed model for the "syncytial tissue triad". According to the concept advanced herein, responses among the vast network of largely-inexcitable corporal smooth muscle cells (nominally the final effectors of erectile capacity) are primarily coordinated by a triumvirate of mechanisms: (1) Transduction—those intracellular processes that occur following cellular activation (i.e, intracellular signal transduction pathways); (2) Propagation—those processes that permit cells which are not directly activated by a locally-restricted neural or hormonal signal to contribute to the ensuing tissue response (erection) (i.e., intercellular communication through gap junctions); and (3) Innervation—those characteristics of the effector neural pathways in the penis that are responsible for initiating both erection and detumescence (i.e., innervation density, firing rate, etc.).

FIGS. 14(A–B): FIG. 14A shows that a macroscopic junctional current ($i_j$) (shown on the bottom), during a 2.5-sec pulse of 10 mV steps to ±100 mV (shown on top), undergoes a time-dependent decay when transjunctional voltage ($V_j$) exceeds ±50 mV. Each voltage pulse was followed by a 5-sec recovery interval. Currents were low pass-filtered at a frequency of 1000 Hz, and digitized at 4 kHz. In FIG. 14B, the instantaneous (inst) and steady-state (ss) $i_j$ for the experiments shown in FIG. 14A were plotted as a function of $V_j$. The instantaneous $i_j$—$V_j$ relationships were approximately linear during the ±100 mV pulses, with a slope conductance of 15.4 nS. The steady-state $i_j$—$V_j$ relationships deviated from linearity above ±50 mV.

FIG. 15 illustrates the steady-state functional conductance-voltage relationships of human bladder smooth muscle (HBSM) cell pairs. Shown are ratios of steady-state (ss) to instantaneous (inst) conductance ($G_j$), taken from eleven HBSM cell pairs, with voltage protocols identical to those described in the previous figure. Each point represents a normalized $G_j$ at corresponding $V_j$ values. $G_j$ declines symmetrically in both $V_j$ directions, with the greatest decrease in $G_j$ occurring when $V_j$ exceeds ±50 mV. The solid lines depict the theoretical fit of the data, assuming a two-state Boltzmann distribution (see Experimental Details Section).

FIGS. 16(A–C): FIG. 16A shows whole-cell current from a cultured HBSM cell pair during a −30 mV voltage step that was applied to cell 1 from a holding potential of 0 mV. The junctional current appeared as equal amplitude and opposite polarity signals. (Only the junctional current trace was displayed in the figure). Here, a 70-sec segment of 180-sec recording is illustrated, and three distinct current levels (closed, open current level 1, and open current level 2) are labeled. The current trace was low pass-filtered at 100 Hz, and digitized at 1 kHz. FIG. 16B shows an all-points amplitude histogram compiled from the junctional current trace. The three distinct peaks correspond to the three current levels labeled above, with open currents of 4.4 and 2.67 pA. The open probability, calculated by fitting the histogram, was 0.76, and there was a total of 34 channel events, with a channel mean open time of 3772 msec. FIG. 16C shows the composed single-channel current-voltage relationships for 8 cell pairs, with a slope conductance of 126 pS.

FIGS. 17(A–B)

FIGS. 18(A–C)

FIG. 19 depicts schematically the mechanistic basis for the direct and indirect integral roles played by $K^+$ channels and gap junctions in modulating contraction and relaxation responses in smooth muscle cells. Potassium currents are depicted in a general (macroscopic) fashion here.

FIG. 20 depicts the results of $K_{ATP}$ gene therapy experiments to treat erectile dysfunction. Retired breeder Sprague-Dawley rats (all 500 g) were transfected with Kir6.2/pcDNA naked DNA, through a single intracavernous injection of 100 μg Kir6.2/pcDNA in 200 μl PBS. One week later, erectile capacity was assessed in vivo, as described in the Experimental Details Section. As illustrated, the results were dramatic and quite similar to the results for the pcDNA/hSlo experiments. At all levels of current stimulation, the Kir6.2/pcDNA-transfected animals, relative to age-matched control animals, showed dramatically-increased intracorporal pressure responses to the same level of current stimulation ($p<0.05$ for all stimulation levels; data shown as the Mean S.E.M.). Since there is no detectable effect of the vector alone, i.e., pcDNA alone, it appears that genetic modification of corporal smooth muscle cells with the Kir6.2 channel gene is also a viable candidate for a gene therapy approach to the treatment of erectile dysfunction.

FIGS. 21(A–B): FIGS. 21A and 21B summarize cystometric data which demonstrate the bladder instability created by urethral obstruction. FIG. 21A depicts micturition reflexes, at regular intervals in the normal rat bladder, which are caused by continuous infusion. Very few spontaneous contractions are seen. FIG. 21B shows an increase in spontaneous contractions in obstructed bladder.

DETAILED DESCRIPTION OF THE INVENTION

Figure 1:
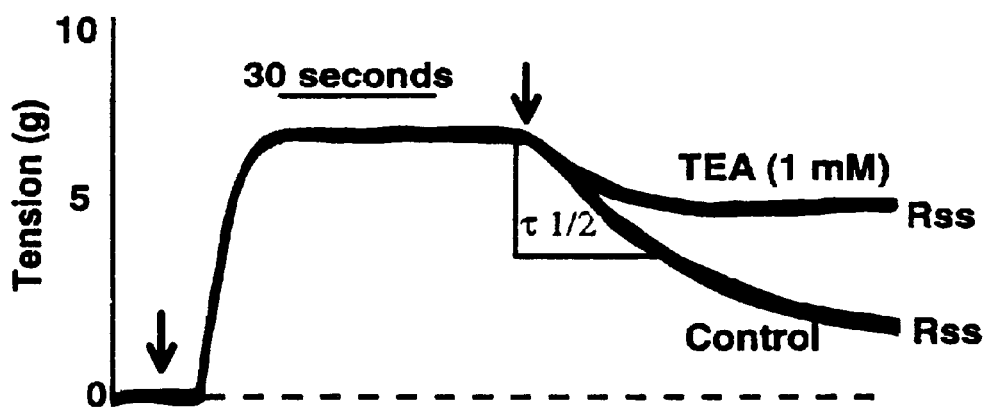
FIG. 1.

The present invention provides a method of gene therapy for treating physiological dysfunctions of smooth muscle through the delivery into, and expression in, a smooth muscle cell of a DNA sequence encoding a protein involved in the regulation of smooth muscle tone. As used herein, "regulation" is the modulation of relaxation or the modulation of contraction.

Examples of smooth muscle cells for which the present method of gene therapy may be used include, but are not limited to, visceral smooth muscle cells of the bladder, bowel, bronchi of the lungs, penis (corpus cavernosum), prostate gland, ureter, urethra (corpus spongiosum), urinary tract, and vas deferens, as well as the smooth and/or skeletal muscle cells of the endopelvic fascia. Specifically, the claimed method of gene therapy may be used in bladder smooth muscle cells, colonic smooth muscle cells, corporal smooth muscle cells, gastrointestinal smooth muscle cells, prostatic smooth muscle, and urethral smooth muscle. Given the many gross histological and physiological similarities in the factors that regulate the tone of smooth muscle tissue and of other vascular tissue, it follows naturally that similar principles would permit the application of the present method of gene therapy to the arterial smooth muscle cells of the bladder, bowel, bronchi of the lungs, penis (corpus cavernosum), prostate gland, ureter, urethra (corpus spongiosum), urinary tract, and vas deferens.

The DNA sequence of interest may be introduced into a smooth muscle cell by a number of procedures known to one skilled in the art, such as electroporation, DEAE Dextran, monocationic liposome fusion, polycationic liposome fusion, protoplast fusion, DNA-coated microprojectile bombardment, creation of an in vivo electrical field, injection with recombinant replication-defective viruses, homologous recombination, and naked DNA transfer by, for example, intravesical instillation. It is to be appreciated by one skilled in the art that any of the above methods of DNA transfer may be combined.

In a preferred embodiment of the invention, the DNA is transferred into the smooth muscle cells by naked DNA transfer, using a mammalian vector. "Naked DNA" is herein defined as DNA contained in a non-viral vector. The DNA sequence may be combined with a sterile aqueous solution, which is preferably isotonic with the blood of the recipient. Such a solution may be prepared by suspending the DNA in water containing physiologically-compatible substances (such as sodium chloride, glycine, and the like), maintaining a buffered pH compatible with physiological conditions, and rendering the solution sterile. In a preferred embodiment of the invention, the DNA is combined with a 20–25% sucrose-in-saline solution, in preparation for introduction into a smooth muscle cell.

Where the DNA is transferred into smooth muscle cells of the bladder, it is introduced into the bladder by intravesical instillation, which is a well-established therapy for the treatment of bladder tumors. The DNA solution is then voluntarily withheld by the patient, within the bladder, for a prescribed duration of time. In another embodiment, the DNA is introduced into the endopelvic fascia, prostate, ureter, urethra, upper urinary tract, or vas deferens by instillation or injection therapy, and the ureter, urethra, or upper urinary tract is obstructed so that the DNA solution remains in contact with the internal epithelial layer for a prescribed period of time. The DNA sequence for expression may also be incorporated into cationic liposomes and directly injected into the smooth muscle cells of the subject.

The present invention specifically provides a method of gene therapy wherein the protein involved in the regulation of smooth muscle tone modulates relaxation of smooth muscle. Representative proteins which modulate relaxation include, for example, connexin 43, nitric oxide synthase (NOS), guanylate cyclase, adenylate cyclase, protein kinase G, protein kinase A, potassium channels (particularly the $K_{ATP}$ and maxi-K subtypes), calcium channels, and any combination thereof. These proteins will enhance relaxation of smooth muscle, and will also decrease smooth muscle tone. In particular, where vasorelaxation is enhanced in penile smooth muscle, an erection will be more easily attained.

Similarly, where smooth muscle tone is decreased in the bladder, bladder capacity will be increased. In this embodiment of the invention, the gene therapy method is particularly useful for treating individuals with bladder hyperreflexia. As used herein, a "hyperreflexic bladder" is one which contracts spontaneously so that an individual is unable to control the passage of urine. This urinary disorder is more commonly called urge incontinence, and may include urge incontinence combined with stress incontinence.

Further provided by the present invention is a method of gene therapy wherein the protein involved in the regulation of smooth muscle tone modulates contraction of smooth muscle. Representative proteins which modulate contraction include, for example, connexin 43, the alpha-1 receptor or the endothelin-1 receptor, phospholipase C, diacylglycerol, protein kinase C, myosin light-chain kinase, calmodulin, potassium channels, calcium channels, and any combination thereof Specific examples of potassium-channel proteins which may be employed are the $K_{ATP}$ and maxi-K subtypes. These proteins can be altered to increase smooth muscle tone. Increased smooth muscle tone will, for example, increase a person's capacity to empty the urine contents from an atonic bladder. As used herein, an "atonic bladder" is one which has diminished capacity to empty its urine contents because of ineffective detrusor contractility.

It is to be understood that the method of gene therapy described by the present invention may involve the transfer into a smooth muscle cell, whose function is involved in contraction and/or relaxation, of more than one nucleic acid sequence encoding a protein. For example, the method of gene therapy may involve the transfer of a nucleic acid encoding protein kinase C, and the previous, simultaneous, or subsequent transfer of a nucleic acid encoding connexin 43. Connexin 43 is a gap-junction protein, found in bladder smooth muscle cells, corporal smooth muscle cells, and many other smooth muscle cell types, which facilitates the interactions between smooth muscle cells. Thus, the addition of nucleic acid encoding connexin 43 will facilitate intercellular interactions so that a greater percentage of cells will be affected by the gene therapy.

Also contemplated for use in the method of the present invention is a DNA sequence that encodes a protein that acts to inhibit a protein that modulates contraction of smooth muscle. A representative protein that modulates contraction of corporal smooth muscle, for example, is protein kinase C. Proteins which inhibit those proteins that are involved in the contraction of smooth muscle will ultimately cause enhanced smooth-muscle relaxation. This relaxation will, for example, result in a decreased capacity to empty the bladder of its urine contents, or in a more easily-attained erection.

Further contemplated is a DNA sequence that encodes a protein that acts to inhibit a protein that modulates relaxation of smooth muscle. An example of a protein that modulates relaxation of smooth muscle is protein kinase A. Proteins which inhibit those proteins that are involved in the relaxation of smooth muscle will ultimately cause enhanced smooth-muscle contraction; this will, for example, increase a person's capacity to empty the contents of an atonic bladder.

Additionally, the present invention specifically provides a method of regulating penile smooth muscle tone in a subject, comprising the introduction, into penile smooth muscle cells of the subject, of a DNA sequence encoding a protein involved in the regulation of smooth muscle tone, and expression in a sufficient number of penile smooth muscle cells of the subject to induce penile erection in the subject. In this embodiment, the method of the present invention is used to alleviate erectile dysfunction. The erectile dysfunction may result from a variety of disorders, including neurogenic, arteriogenic, and veno-occlusive dysfunctions, as well as other conditions which cause incomplete relaxation of the smooth muscle. The subject may be animal or human, is preferably human.

Furthermore, the present invention specifically provides a method of regulating bladder smooth muscle tone in a subject, comprising the introduction, into bladder smooth muscle cells of the subject, of a DNA sequence encoding a protein involved in the regulation of smooth muscle tone, and expression in a sufficient number of bladder smooth muscle cells of the subject to enhance bladder relaxation in the subject. In this embodiment, the method of the present invention is used to alleviate a hyperreflexic bladder. A hyperreflexic bladder may result from a variety of disorders, including neurogenic and arteriogenic dysfunctions, as well as other conditions which cause incomplete relaxation or heightened contractility of the smooth muscle of the bladder. The subject may be animal or human, and is preferably human.

Additionally, the present invention specifically provides a method of regulating bladder smooth muscle tone in a subject, comprising the introduction into smooth muscle cells of the subject of a DNA sequence encoding a protein involved in the regulation of smooth muscle tone, and expression in a sufficient number of smooth muscle cells of the subject to induce bladder contraction in the subject. In this embodiment, the method of the present invention is used to alleviate an atonic bladder. An atonic bladder may result from a variety of disorders, including neurogenic and arteriogenic dysfunctions, as well as other conditions which cause incomplete contraction of the smooth muscle of the bladder. A neurogenic bladder dysfunction may manifest itself as partial or complete urinary retention or overflow incontinence. Examples of neurogenic dysfunctions of the bladder include a hypotonic, or flaccid, bladder, and a spastic, or contracted, bladder. These dysfunctions may result from an abnormality, injury, or disease process of the brain, spinal cord, or local nerve supply to the bladder and its outlet. Disease processes that result in neurogenic bladder dysfunction include benign hyperplasia of the prostate gland (BHP); cerebrovascular accidents; demyelinating or degenerative diseases, such as multiple sclerosis and amyotrophic lateral sclerosis; diabetes mellitus; a ruptured intervertebral disk; syphilis; and brain or spinal cord tumors. Again, the subject may be animal or human, and is preferably human.

In a further embodiment, the method of the present invention is used to prevent hypertrophy of the bladder smooth muscle of a subject, as caused by BHP, by introducing into the prostate of the subject a DNA sequence encoding a protein involved in the regulation of smooth muscle tone. BHP is thought to be associated with increased tone of the smooth muscle in the prostate stoma. Eventually, BHP results in bladder-outlet obstruction, and hypertrophy of the bladder.

In another embodiment, the method of the present invention is used to induce contraction of the endopelvic fascia of a subject. The endopelvic fascia contributes to the support of the uterus and vagina. Frequently, women who experience a multiple of childbirths become incontinent due to stress damage between the endopelvic fascia and the muscles of the urethra.

In addition, the present invention provides for a method of reducing inflammation and irritation of smooth muscle in a subject, comprising the introduction, into the smooth muscle cells of the subject, of a DNA sequence encoding a protein involved in the regulation of smooth muscle tone, and expression in a sufficient number of smooth muscle cells of the subject to reduce the effects of inflammation and irritation. For example, the method provided by the present invention may be used to reduce the symptoms of interstitial cystitis of the bladder. Interstitial cystitis is a condition of the bladder that has clinical manifestations of inflammation and irritation. The interstitial cystitis may be caused, for example, by an allergic reaction, an autoimmune disease, or a collagen disease. Furthermore, the method of gene therapy provided herein may be used, for example, to reduce inflammation and irritation of the ureter, urethra, or urinary tract of a subject, which may be caused by a bacterial, fungal, or parasitic infection.

Also contemplated by the present invention is a method of inducing smooth muscle tone in a subject who has undergone reanastomosis of the vas deferens, comprising the introduction, into the smooth muscle cells of the subject, of a DNA sequence encoding a protein involved in the regulation of smooth muscle tone, and expression in a sufficient number of smooth muscle cells of the subject to alter smooth muscle tone in the vas deferens of the subject and ensure propulsion of the contents of the vas deferens.

In other embodiments of the invention, the method of gene therapy described herein is used to treat other dysfunctions relating to the performance of smooth muscle, including, but not limited to, asthma; coronary artery disease (infused during angiography); genitourinary dysfunctions of the ureter, urethra, urinary tract, and vas deferens; irritable bowel syndrome; migraine headaches; premature labor; Raynaud's syndrome; and thromboangitis obliterans. When used to treat asthma, the present method of gene therapy may be administered to a subject by way of aerosol delivery using any method known in the art.

The present invention also provides viral and non-viral recombinant vectors. A viral-based vector comprises: (1) nucleic acid of, or corresponding to at least a portion of, the genome of a virus, which portion is capable of directing the expression of a DNA sequence; and (2) a DNA sequence encoding a protein involved in the regulation of smooth muscle tone, operably linked to the viral nucleic acid and capable of being expressed as a functional gene product in the target cell. The recombinant viral vectors of the present invention may be derived from a variety of viral nucleic acids known to one skilled in the art, e.g., the genomes of adenovirus, adeno-associated virus, HSV, Semiliki Forest virus, vaccinia virus, and other viruses, including RNA and DNA viruses.

The recombinant vectors of the present invention may also contain a nucleotide sequence encoding suitable regulatory elements, so as to effect expression of the vector construct in a suitable host cell. As used herein, "expression" refers to the ability of the vector to transcribe the inserted DNA sequence into mRNA so that synthesis of the protein encoded by the inserted nucleic acid can occur. Those skilled in the art will appreciate the following: (1) that a variety of enhancers and promoters are suitable for use in the constructs of the invention; and (2) that the constructs will contain the necessary start, termination, and control sequences for proper transcription and processing of the DNA sequence encoding a protein involved in the regulation of smooth muscle tone, upon introduction of the recombinant vector construct into a host cell.

The non-viral vectors provided by the present invention, for the expression in a smooth muscle cell of the DNA sequence encoding a protein involved in the regulation of smooth muscle tone, may comprise all or a portion of any of the following vectors known to one skilled in the art: pCMVβ (Invitrogen), pcDNA3 (Invitrogen), pET-3d (Novagen), pProEx-1 (Life Technologies), pFastBac 1 (Life Technologies), pSFV (Life Technologies), pcDNA2 (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVl1392 (Invitrogen), pCDM8 (Invitrogen), pcDNA I (Invitrogen), pcDNA I(amp) (Invitrogen), pZeoSV (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors would be apparent to one skilled in the art.

Promoters suitable for the present invention include, but are not limited to, constitutive promoters, tissue-specific promoters, and inducible promoters. In one embodiment of the invention, expression of the DNA sequence encoding a protein involved in the regulation of smooth muscle tone is controlled and affected by the particular vector into which the DNA sequence has been introduced. Some eukaryotic vectors have been engineered so that they are capable of expressing inserted nucleic acids to high levels within the host cell. Such vectors utilize one of a number of powerful promoters to direct the high level of expression. Eukaryotic vectors use promoter-enhancer sequences of viral genes, especially those of tumor viruses. This particular embodiment of the invention provides for regulation of expression of the DNA sequence encoding the protein, through the use of inducible promoters. Non-limiting examples of inducible promoters include metallothionine promoters and mouse mammary tumor virus promoters. Depending on the vector, expression of the DNA sequence in the smooth muscle cell would be induced by the addition of a specific compound at a certain point in the growth cycle of the cell. Other examples of promoters and enhancers effective for use in the recombinant vectors of the present invention include, but are not limited to, CMV (cytomegalovirus), SV40 (simian virus 40), HSV (herpes simplex virus), EBV (Epstein-Barr virus), retrovirus, adenoviral promoters and enhancers, and smooth-muscle-specific promoters and enhancers. An example of a smooth-muscle-specific promoter is SM22α.

The present invention further provides a smooth muscle cell which expresses an exogenous DNA sequence encoding a protein involved in the regulation of smooth muscle tone. As used herein, "exogenous" means any DNA that is introduced into an organism or cell. The introduction into the smooth muscle cell of a recombinant vector containing the exogenous DNA sequence may be effected by methods known to one skilled in the art, such as electroporation, DEAE Dextran, cationic liposome fusion, protoplast fusion, DNA-coated microprojectile bombardment, injection with recombinant replication-defective viruses, homologous recombination, and naked DNA transfer by, for example, intravesical instillation. It will be appreciated by those skilled in the art that any of these methods of DNA transfer may be combined.

Importance of Potassium Channels

Alterations in ion-channel activity are suspected in the etiology of human smooth-muscle-related disorders as diverse as asthma, bladder dysfunction, erectile dysfunction, and hypertension. In all of these tissues, myocyte potassium channels play a central role in mediating the effects on smooth muscle tone of diverse endogenous substances. While many $K^+$ channels are present in human smooth muscle cells, the $K_{Ca}$ (or maxi-K) channel subtype plays a pivotal role in modulating contraction and relaxation responses; thus, it also plays a role in determining the degree of smooth muscle tone. For example, it is suspected that $K^+$ channels participate in the disease process of incontinence, a condition related to bladder over-activity (i.e., increased detrusor contractility) that affects the quality of life of millions of Americans (Brading, A. F., *Jap. J. Pharmacol.*, 58(2):120P–127P, 1992; Andersson, K.-E., *Urol.*, 50:74–84, 1997; and Fry, et al., *Exper. Physiol.*, 84:161–69, 1999).

Potassium channels are important in the regulation of human smooth muscle tone. Genes for more than thirty $K^+$ channels, many of which are expressed in smooth muscle, have been identified (Lawson, K., *Clinical Science*, 91:651–63, 1996; Lawson, K., *Pharmacol. Ther.*, 70(1):39–63, 1996; and Ashcroft, F. M., ed., *Ion Channels and Disease: Channelopathies*, New York: Academic Press, 2000). As one might imagine, the existence of such a diverse repertoire of $K^+$ channels has potentially-important implications for the modulation of electrical activity in human smooth muscle cells, including corporal myocytes. Despite the plethora of known $K^+$-channel subtypes, experimental and clinical data in human corporal smooth muscle provide evidence for the presence and physiological relevance of only two: (1) the metabolically-gated $K^+$ channel (i.e., $K_{ATP}$), and (2) the large-conductance, calcium-sensitive $K^+$ channel (i.e., the $K_{Ca}$ or maxi-K channel) (Dorschner, et al., *Mol. Pharmacol.*, 55(6):1060–66, 1999; Lee, et al., *Int. J. Impotence Res.*, 11:179–88, 1999; and Benevides, et al., *J. Urol.*, 161:212 (Abstract), 1999).

There is substantial evidence from many tissues, including smooth muscle, that the $K_{ATP}$ channel is a heteromultimer, composed of an inward rectifier K⁺-channel subunit (Kir), which is a tetramer of homologous subunits, and a sulfonylurea receptor subunit (SUR), which is the putative target of orally-active sulfonylurea compounds such as glibenclamide. The SUR subunits exist in a 1:1 stoichiometry with the Kir subunits (Aguilar-Bryan, et al., *Physiol. Rev.*, 78:227–45, 1998; Seino, *Annu. Rev. Physiol.*, 61:337–62, 1999; and Dorschner, et al., *J. Pharmacol. Exp. Ther.*, 55:1060–66, 1999). The tetrameric Kir assembly represents the pore-forming region of the $K_{ATP}$ channel; however, importantly, it is not known to form a functional channel in the absence of the SUR subunit.

The Kir gene family has been divided into six subfamilies, based on sequence identity of the cloned channel cDNAs. Major subfamilies of 1.0, 2.0, and 6.0 have been identified. The Kir2.x and Kir6.x are arguably the most relevant to the $K_{ATP}$ channels found in smooth muscle, and, thus far, only Kir6.2 is known to be present in human corporal smooth muscle (Day, et al., FASEB J., 11:A328, 1997). With respect to the SUR subunit, two SUR genes have been identified, SUR1 and SUR2. Splice variants of SUR2 provide for SUR2A, SUR2B, and SUR2C subtypes. There are currently no data available concerning the disposition of the SUR subunit(s) in human corporal myocytes, but such studies are ongoing. Nevertheless, recombination of the Kir6.2 subtype with the SUR2B isoforms yields a $K_{ATP}$-like channel which has pharmacological and electrophysiological characteristics similar to those observed for the putative $K_{ATP}$ channel that is present in human corpus cavernosum smooth muscle (i.e., Kir6.2) (Lee, et aL, *Int J. Impotence Res.*, 11:189–99, 1999).

From a pharmacological standpoint, several K⁺-channel activators (e.g., pinacidil, cromakalim, lemakalim, and nicorandil) have been shown to relax precontracted corporal tissue strips from both animals and humans; moreover, these activators have been shown to elicit an erection in monkeys and humans when injected intracavernosally (Andersson, *Pharmacol. Toxicol.*, 70:244–54, 1992; and Benevides, et al., *J. Urol.*, 161:212(Abstract), 1999). Furthermore, with respect to pinacidil and levcromakalim, relaxation of pre-contracted human corporal tissue strips was shown to be glibenclamide-sensitive (Day, et al., FASEB J., 11:A328, 1997). Consistent with such observations, electrophysiological studies (i.e., patch clamp) conducted on freshly-isolated individual human corporal myocytes have identified two ATP-inhibited, glibenclamide-sensitive unitary currents, of approximately 20 and 60 pS (Lee, et al., *Int. J. Impotence Res.*, 11:189–99, 1999). In addition, a pinacidil-induced, glibenclamide-sensitive whole-cell outward current has been demonstrated on both cultured (Christ, et al., *J. Andrology*, 14:319–28, 1993) and freshly-isolated (Lee, et al., *Int. J. Impotence Res.*, 11:189–99, 1999) human corporal myocytes. The extant evidence, then, is consistent with the notion that the $K_{ATP}$ channel subtype is an important modulator of human corporal smooth muscle tone.

Importance of Gap-junction Proteins

Of critical importance with respect to all in vivo gene therapy approaches are the percentage of target cells that must be affected in order to see a physiologically-relevant therapeutic effect, and the relative efficiency of affecting only the desired cell type(s). In this regard, it is suspected that gene therapy may be inherently more successful in alleviating erectile dysfunction and bladder dysfunction than in treating more systemic, cardiovascular disorders. In particular, the method of gene therapy provided by the present invention meets the need for a method which produces global changes in a tissue by genetically modifying only a fraction of the cells. For example, the inventors have demonstrated the effectiveness of naked DNA transfer in the penis and in the bladder. The inventors have also shown that the physiological functions of a smooth muscle cell enable the intercellular transfer and continuous propagation, in only a fraction of the total cellular population, of the effects of incorporation of naked DNA sequences encoding proteins involved in the regulation of smooth muscle tone. This effect is brought about through the operation of gap-junction proteins.

Figure 2:
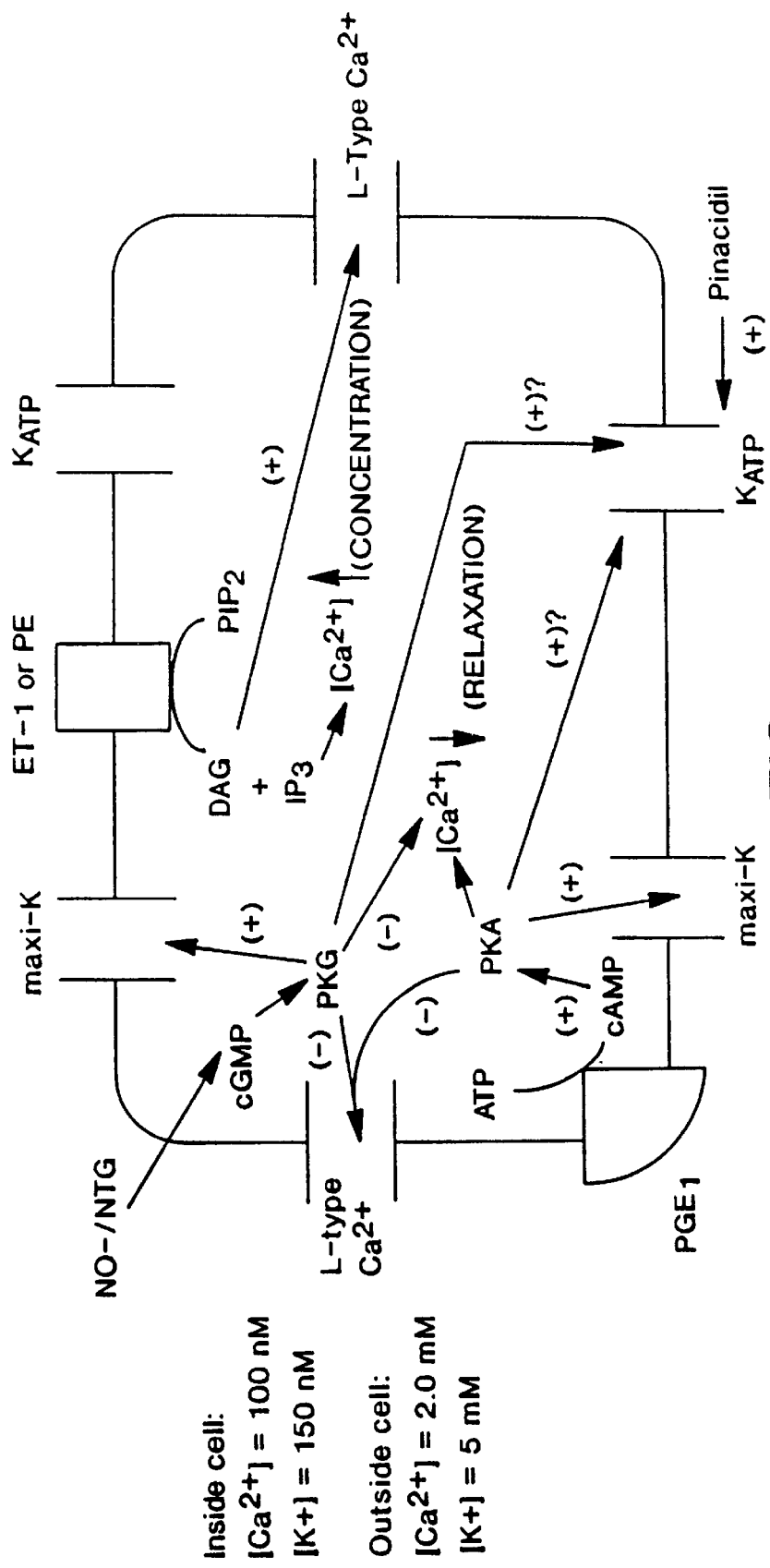
FIG. 2.
Figure 19:
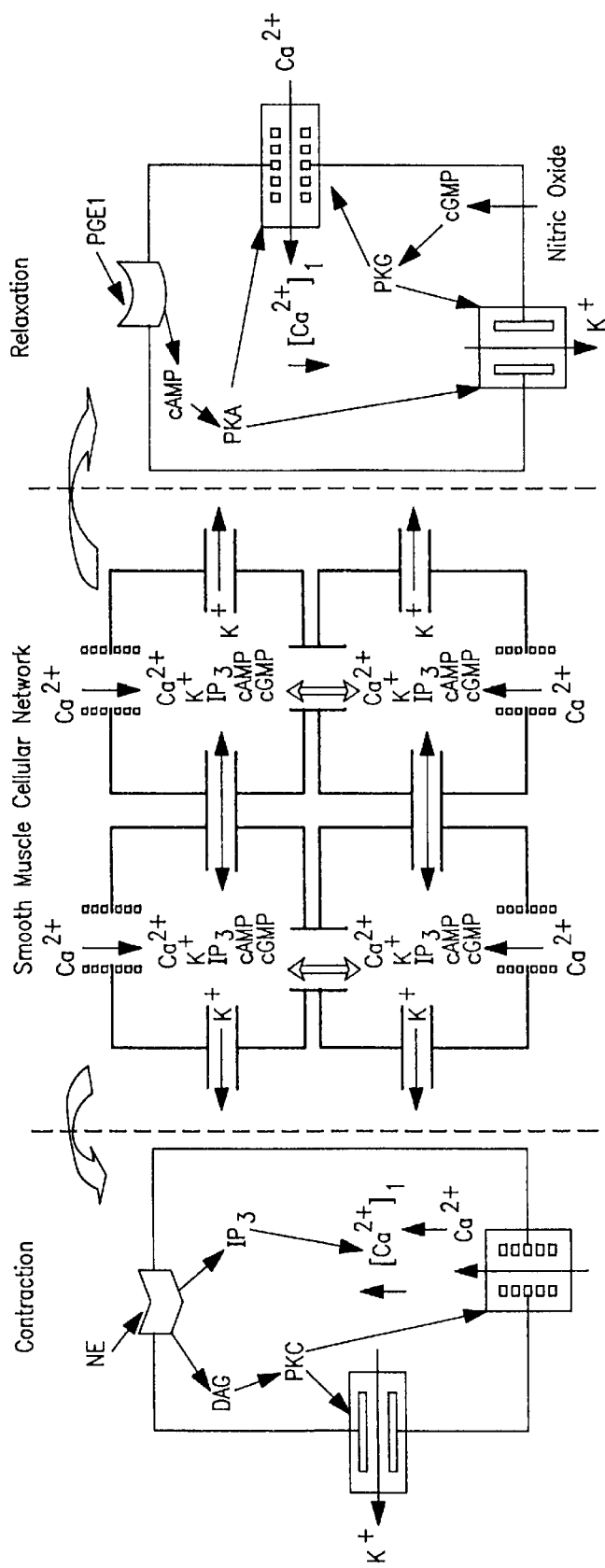
FIG. 19.

It is a well-documented fact that corporal and arterial smooth muscle cells are interconnected, both in vivo and in vitro, by a ubiquitously-distributed population of intercellular channels, known as gap-junction proteins, (Christ, et al., *Life Sciences*, 49(24):PL195–200, 1991; Christ, et al., *International Journal of Impotence Research*, 5(2):77–96, 1993; Christ, et al., *Journal of Pharmacology & Experimental Therapeutics*, 266(2):1054–65, 1993; Christ, et al., *Biophysical Journal*, 67(3):1335–44, 1994; Christ, G. J., *Urological Clinic of North America*, 22(4):727–45, 1995; Christ, et al., *Circulation Research*, 79:631–46, 1996; Christ, G. J., *World Journal of Urology*, 15:36–44, 1997; and Christ and Melman, *Molecular Urology*, 1:45–54, 1997). The mechanisms for these channels in corporal smooth muscle cells are depicted in FIG. 2. Additionally, as illustrated in FIG. 19, gap-junction channels are critical to corporal tissue function and, ultimately, the success of gene therapy for the treatment of erectile dysfunction.

In the corpora, for example, smooth-muscle contraction (i.e., elevation in intracellular calcium levels) might be accomplished following activation of the $\alpha_1$-adrenergic receptor by norepinephrine, or by endothelin-1 (ET-1) activation of the $ET_A$ receptor. In both cases, receptor activation leads to $Ca^{2+}$ mobilization. Specifically, activation of these receptors by norepinephrine or ET-1 leads to activation of phospholipase C, which cleaves membrane-bound phosphatidylinositol ($PIP_2$) into $IP_3$ and diacylglycerol (DAG). As illustrated in FIGS. 1 and 2, increases in DAG and $IP_3$ ultimately exert their effects, at least in part, via increases in intracellular $Ca^{2+}$ levels. Conversely, any physiological event resulting in a diminution of transmembrane $Ca^{2+}$ flux, or sequestration of intracellular $Ca^{2+}$ (e.g., membrane hyperpolarization), will result in smooth-muscle relaxation. For example, prostaglandin $E_1$ ($PGE_1$) activates the $PGE_1$ receptor to stimulate the adenylate cyclase enzyme, which then catalyzes the conversion of ATP to cAMP. Increased cAMP then stimulates protein kinase A (PKA). Alternately, smooth-muscle relaxation can be achieved by nitric oxide, released from endothelial or neuronal sources. Nitric oxide diffuses into smooth muscle cells to activate soluble guanylate cyclase, which catalyzes the conversion of GTP to cGMP. Elevated cGMP levels activate protein kinase G (PKG).

The effects of PKA, PKG, and PKC on gap junctions, K⁺ channels, and $Ca^{2+}$ channels are thought to be mediated through phosphorylation of specific amino acid residues on these target proteins. FIG. 2 illustrates the result of their putative actions, where (+) means a stimulatory, positive, or increasing effect, and (−) means an inhibitory or negative effect. This simplified model demonstrates how the interactions of these important second-messenger systems might impact on gap-junction, K⁺, and $Ca^{2+}$ channels, thereby modulating smooth muscle tone in vitro and in vivo.

K⁺-ion flux in smooth muscle cells is controlled by three main effector pathways. The first two are the cAMP/PKA (protein kinase A) and cGMP/PKG (protein kinase G) pathways, which are activated by $PGE_1$ and nitric oxide (NO), respectively. These pathways clearly modulate the activity of the maxi-K channel; however, their effects on the $K_{ATP}$ channel have not yet been documented. The third pathway involves the $K^+$-channel modulators, which modulate the activity of the $K_{ATP}$ channel. Because of the disposition of these ions in the intracellular and extracellular spaces, the opening of $Ca^{2+}$ channels leads to the influx of $Ca^{2+}$, down its electrochemical gradient, and subsequent intracellular depolarization; the opening of $K^+$ channels leads to efflux of K+, down its electrochemical gradient, and subsequent intracellular hyperpolarization. The effects of these reciprocal pathways on membrane potential and the level of smooth muscle tone are exerted, at least in part, through modulation of the intracellular calcium concentration, where increases in intracellular calcium are associated with contraction, and decreases in intracellular calcium are associated with relaxation.

Connexin 43 is the predominant gap-junction protein isoform expressed in the human and rat penis and bladder. The presence of connexin 43 in human bladder smooth muscle has been documented only by the inventors. Connexin 43 intercellular channels provide partial cytoplasmic continuity between adjacent smooth muscle cells, allowing the intercellular exchange of physiologically-relevant ions ($K^+$ and $Ca^{2+}$) and second-messenger molecules ($IP_3$, cAMP, and cGMP). This is extremely important, given the relatively sparse autonomic innervation of the corporal parenchyma and the parenchyma of other visceral organs.

As demonstrated by both molecular biological and electrophysiological techniques, gap junctions provide the anatomic substrate required for the rapid and syncytial contraction and relaxation responses required of the corporal smooth muscle cells for normal penile erection, as well as detumescence. Moreover, gap junctions provide an additional anatomic substrate for the rapid and syncytial contraction and relaxation responses required of bladder smooth muscle cells in order to achieve normal bladder function. While bladder myocytes are clearly capable of regenerative electrical events, the presence of gap junctions is relevant, not only to provide a "safety factor" for the maintenance and propagation of regenerative electrical events (as shown in the heart), but also for ensuring tissue plasticity. Viewed in terms of the recently-advanced "syncytial tissue triad" concept (see Christ, G. J., *World J. Urol.*, 15:36–44, 1997, herein incorporated by reference), gap junctions are thought to endow the bladder musculature with the ability to function syncytially under a very wide range of physiological conditions, thereby mitigating the sparsity of direct innervations of bladder smooth muscle cells by the autonomic nervous system. Nevertheless, the electrical excitability of the bladder myocyte has been traditionally viewed as a priori evidence for the lack of importance of demonstrable gap junctions between bladder myocytes (using light and electron microscopy).

Perhaps more importantly, however, is the possibility that these gap junctions may provide a mechanistic basis for the efficacy of gene therapy in the treatment of penile dysfunction and bladder dysfunction. In particular, the network of gap junctions permits smooth muscle cells, not directly activated by a relevant neuronal/pharmacological signal, to be rapidly, albeit indirectly, recruited into the contraction or relaxation response by way of this prominent intercellular pathway. The experimental and clinical evidence verifying the validity of this supposition has been outlined in recent publications (Christ, et al., *Circulation Research*, 79:631–46, 1996; and Christ, G. J., *World J. Urol.*, 15:36–44, 1997), and a mathematical model has been constructed that accounts for this behavior (Christ, et al., *J. Urol.* 155:620A (Abstract), 1996; and Ramanan, et al., *Journal of Theoretical Biology*, 193(1):69–84, 1998).

Thus, as the inventors have demonstrated for the penis and the bladder, the major implication is that the presence of these gap-junction channels makes it likely that only a small fraction of the smooth muscle cells need to be genetically modified in order to effect rather global changes in penile or bladder smooth muscle tone. The inventors have already demonstrated that the gap-junction protein connexin 43, as well as two prominent $K^+$-channel subtypes (i.e., the maxi-K and $K_{ATP}$ channels), are present in rat and human penis and bladder smooth muscle. Accordingly, both the penis and bladder are amenable to the gene-therapy protocols proposed in this application, and are the first logical targets for evaluating the efficacy of genetic modulation of smooth muscle tone.

Effect of Gene Therapy on Organ Systems

Smooth muscle cells constitute a heterogeneous collection of effector cells. By virtue of their presence in, and regulation of, blood vessels, they ultimately affect the function of all organs. Moreover, they are the parenchymal cells in most hollow organs, including the viscera of the urogenital tract (i.e., bladder, ureter, and prostate). Everywhere, including the entire genitourinary system, coordination of activity among the smooth muscle cells is an important component of normal tissue function and, therefore, organ function. While the autonomic nervous system supplies neural input to all peripheral organs, the density, distribution, and roles of nerve fibers vary. In a given tissue, the level of activity of smooth muscle cells, and the cellular mechanisms involved, can differ dramatically from those of other smooth muscle phenotypes.

It is becoming increasingly clear that the role of the autonomic nervous system in particular organs is uniquely correlated with the physiological phenotype of the constituent smooth muscle cells. Membrane excitability, signal transduction processes, and the extent of cell-to-cell communication between smooth muscle cells all vary among different tissues. Thus, the components of an effector process are integrated together to yield the characteristic action of an organ. Furthermore, the components occur in different combinations to provide a rich diversity of organ function. Understanding the principles of initiation and spread of stimuli in the smooth muscle tissues is clearly necessary for understanding organ physiology, and, as discussed below, provides the key to the success of gene therapy.

It is of particular relevance that the functional diversity of smooth muscle correlates with the functional diversity of peripheral organ systems. This diversity is expressed at every level of tissue organization within an organ, from the pattern of autonomic neuronal innervation, to the phenotype of the parenchymal cell. Much of the diversity in smooth muscle function is due to the effector systems that transduce the results of receptor activation into intracellular second-messenger events throughout the tissue. Clearly, such diversity of smooth muscle regulation/function has important implications for smooth-muscle-specific therapeutic options. However, it is necessary also to consider the mechanism(s) by which signals are integrated among the parenchymal cells. In particular, the success of the method of gene therapy described in this application depends on the more recent evidence documenting the distribution and function of gap junctions between smooth muscle cells in organ systems throughout the body. This evidence points to a major role for intercellular communication in coordinating smooth muscle responses in the various tissues of the different organs.

The principles outlined above suggest that the use of gene therapy to treat disorders of the urogenital system will overcome one of the significant barriers to clinical success that arises when gene therapy is used to treat many other diseases, including cancer and cardiovascular disease. In particular, when used to treat cancer and cardiovascular disease, gene therapy explicitly depends on high-efficiency transfection rates in selected cells, following systemic administration. As such, then, the use of gene therapy in the treatment of cancer or cardiovascular disease stands in stark contrast to the use of gene therapy to treat impotence or incontinence, where the isolated, easily-accessible conditions of the penis and bladder confer distinct advantages to the selective administration of genetic material.

For example, it appears that gene therapy is an attractive possibility for the treatment of erectile dysfunction in the human penis because the presence of pharmacologically-induced erections in many impotent men indicates that the veno-occlusive mechanism is properly functioning in these patients. In such patients, then, an erection could be pharmacologically induced by conventional intracavernous agents, while the gene(s) of interest are simultaneously injected. The injected gene(s) would be expected to be restricted largely to the corporal parenchyma, because the venous outflow during a normal erection is very small (Lue, et al., *J. Urol.*, 137:829, 1987; Carrier, et al., *J. Urol.*, 42(4):468–81, 1993; Lerner, et al., *J. Urol.*, 149(5.2):1246–55, 1993; and Andersson, et al., *Physiological Reviews*, 75(1):191–236, 1995). In this scenario, there would be little risk of systemic vascular side effects.

Similarly, the anatomical location of the human bladder makes gene therapy an attractive possibility because, as with the human penis, the bladder is a relatively "isolated" organ system that should be quite amenable to genetic modification, in the absence of effects on other organs/tissues. The bladder is an internal organ into which external substances can be easily introduced through a urethral catheter. Bacillus Calmette-Guerin (BCG) therapy for bladder cancer is already a well-recognized use of this technique. The instillation of a gene product in an aqueous solution, which can be voluntarily retained by the patient within the bladder for a prescribed duration of time, would presumably restrict the gene product largely to the bladder musculature. The data described in the Experimental Details Section document that this is, indeed, the case. Again, in this scenario, there is clearly little risk of systemic side effects.

FIGS. 14–18 document the presence in human bladder smooth muscle cells of the requisite cellular components that make the bladder an attractive organ for gene therapy, either primary or secondary (i.e., in association with subsequent selective pharmacological manipulation). As illustrated in the figures, the gap-junction protein, connexin 43, is an integral component of the human bladder smooth muscle cell.

As proposed herein, the goal of gene therapy in the urogenital system is to achieve the lowest transfection rate possible that is correlated with the desired physiological changes. Taken together, it is clear that less aggressive and less invasive genetic strategies, such as a single injection of naked DNA, are attractive options for the effective treatment of urogenital diseases. Previous physiological studies in the rat penis (Rehman, et al., *Am. J. Physiol.*, 41:H1960–71, 1997) have confirmed this supposition, and, therefore, have assisted in establishing the boundary conditions for the maintenance of normal integrative tissue responses.

Moreover, the parameters/conditions for normal tissue behavior, which the inventors have identified thus far, have been recently encapsulated in a mathematical construct (Ramanan, et al., *Journal of Theoretical Biology*, 193(1):69–84, 1998). The resulting mathematical model can be used to generate experimentally-testable and clinically-testable hypotheses concerning the predicted behaviors of tissues under a diverse range of physiologically-relevant conditions. The model will assist, for example, in determining the lower limit of transfection efficiency required to achieve restoration of normal tissue function in a urogenital organ compromised by disease. It will also assist in identifying the best probes/genes for the transfection.

The inventors anticipate that gene therapy alone (i.e., the proposed genetic alteration of the smooth muscle cells' response to their environment), will work in all patients in whom there is enough neuronal innervation remaining to coordinate a normal syncytial tissue response. However, in those patients in whom sufficient neuronal innervation is not available to guarantee the success of gene therapy per se, the inventors have proposed a secondary strategy. The secondary strategy involves the concomitant administration of either orally-active agents, or locally-administered drugs (e.g., the MUSE intraurethral suppository), that will augment the underlying effects of gene therapy (in particular, penile erection or bladder function).

For example, one could transfect the penile or bladder smooth muscle cells with a $K^+$ channel, as proposed herein, and then deliver to the patient a drug which selectively activates that channel. There are many possible combinations of custom-designed drugs and/or genetically-engineered $K^+$ channels that could produce a similar desired effect. Another example of such a secondary, or combined genetic/pharmacologic, therapy would be the transfection of the penis or bladder with a maxi-K or $K_{ATP}$ channel subtype/isoform/chimera, followed by administration to the patient of a selective/synthetic activator of that channel. The foregoing two examples represent merely the most obvious of a plethora of potential therapeutic possibilities.

In summary, the method of gene therapy provided by the present invention is designed to take advantage of the generally-accepted physiological principle that relatively subtle alterations in the balance between contracting and relaxing stimuli can result in profound alterations in smooth muscle physiology, and, therefore, smooth muscle function (Christ, et al., *British Journal of Pharmacology*, 101(2):375–81, 1990; Azadzoi, et al., *J. Urol.*, 148(5):1587–91, 1992; Lerner, et al., *J. Urol.*, 149(5.2):1246–55, 1993; Taub, et al., *J. Urol.*, 42:698, 1993; and Christ, G. J., *Urological Clinics of North America*, 22(4):727–45, 1995). When using the method of gene therapy described herein, the goal is to restore a more normal balance between contracting and relaxing stimuli following expression of exogenous genes that code for physiologically-relevant proteins in smooth muscle. As indicated in regard to the rat model, expression of these exogenous genes can be maintained for a period of weeks to months. This would permit the patient to obtain a "normal" erection, or "normal" bladder function, in the absence of any other exogenous manipulation, during this time period. Clearly, this is a major advance over all currently-available therapies. Indeed, the accessibility of the urogenital organs, the documented presence of gap junctions among smooth muscle cells throughout the urogenital tract, and the fact that subtle alterations in the tone of smooth muscle are responsible for many aspects of human urogenital disease, all provide clear advantages to the use of gene therapy for treating urogenital disorders.

The present invention is described in the following Experimental Details Section. That section is set forth to aid in the understanding of the invention, and should not be construed to limit in any way the invention as defined in the claims which follow thereafter.

Experimental Details Section

Materials and Methods

I. Erectile Dysfunction Gene Therapy Experiments

The discussion which follows outlines two specific strategies for gene therapy of erectile dysfunction. In the first case, the "sensitivity" of the smooth muscle cells was nominally enhanced to the endogenous neuronal stimulus by transfecting the cells with the human maxi-K cDNA. In the second case, the neuronal "driving force" for erection was increased by transfecting corporal smooth muscle cells with a constitutively-expressed nitric oxide synthase (NOS) cDNA, bNOS. Clearly, this strategy for gene therapy is explicitly dependent on both the efficacy and stability of the proposed transfection. Evidence for both is presented below. Additionally, in order to examine the potential utility of gene therapy involving the $K_{ATP}$ channel in treating erectile dysfunction and bladder incontinence, the inventors examined the ability of a single intracavernous injection of 100 g of Kir6.2/pVax1 to restore the compromised erectile capacity normally associated with aging in the Sprague-Dawley male retired breeder.

a) Gene Transfer of Maxi-K Using a Recombinant Vector

1. Plasmids and genes

The pCMVβ and pcDNA3 plasmids were purchased from Invitrogen (San Diego, Calif.). The human cDNA of hSlo, the α- or pore-forming subunit of maxi-K, was obtained from Dr. Salkoff (Washington University School of Medicine, St. Louis, Mo.) (McCobb, et al., *American Journal of Physiology*, 269:H767–H777, 1995). The nucleotide sequence of the hSlo cDNA is also available at Genbank Accession No. U23767. The neuronal nitric oxide synthase (NOS) cDNA was obtained from Dr. S. Snyder (Johns Hopkins University) and Dr. D. Bredt (Univ. Calif. San Francisco) (Bredt, et al., *Nature*, 351:714–18, 1991). The nucleotide sequence of the neuronal NOS is also available at Genbank Accession No. X59949. The human maxi-K channel cDNA (approximately 3,900 nucleotides, or 3.9 kb, long) (McCobb, et al., *American Journal of Physiology*, 269:H767–H777, 1995) or the neuronal NOS cDNA (Bredt/Snyder 91287795) (Bredt, et al., *Nature*, 351:714–18, 1991) was inserted into the XhoI-XbaI cloning sites of the pcDNA3 vector, where expression is driven off the cytomegalovirus CMVβ promoter (Invitrogen). One hundred µg of plasmid DNA was suspended in 200 µl of sterile phosphate-buffered saline (PBS) containing 20% sucrose, then injected into the corpus cavernosum (CC) of anesthetized rats.

2. Demographics of experimental animals

A total of 74 male Sprague-Dawley rats (Taconic Farms, Germantown, N.Y.) were used in the following studies. Twenty-nine of these animals were 10–20 weeks old, and weighed 200–250 g; five of these served as the young control animals. The remaining 45 animals, which were purchased as retired breeders, ranged in weight from 500–700 g. All rats were fed Purina lab rodent chow ad libitum, and housed individually with a 07:00–19:00 light cycle. The demographics of the animal population, with respect to protocol enrolment, are displayed in Table 1.

TABLE 1

Gene Transfer and Time Course Experiments

| Group | Rats | Age | Gene Therapy | Method of Gene Transfer | Time Course Experiments |
|---|---|---|---|---|---|
| A | n = 12 | 10 weeks | LacZ (n = 9) | Adenovirus (n = 3) Liposome (n = 3) Naked DNA (n = 3) | |
| | | | Control (n = 3) | | |
| B | n = 24 | 10 weeks | LacZ (n = 12) | Naked DNA | 2 week (n = 3) 4 week (n = 3) 8 week (n = 3) 12 week (n = 3) |
| | | | Control (n = 12) | (Sham) | 2 week (n = 3) 4 week (n = 3) 8 week (n = 3) 12 week (n = 3) |
| C | n = 20 | 20 weeks | NOS (n = 12) | Naked DNA | 1 month (n = 2) 2 month (n = 4) 3 month (n = 4) 4 month (n = 2) |
| | | | Control (n = 8) | (Sham) | 1 month (n = 2) 2 month (n = 2) 3 month (n = 2) 4 month (n = 2) |
| D | n = 18 | 20 weeks | Maxi-K (n = 10) | Naked DNA | 1 month (n = 2) 2 month (n = 4) 3 month (n = 2) 4 month (n = 2) |
| | | | Control (n = 8) | (Sham) | 1 month (n = 2) 2 month (n = 2) 3 month (n = 2) 4 month (n = 2) |

3. Techniques for gene transfer of LacZ into smooth muscle cells - Group A

Gene transfer into vascular smooth muscle cells has been achieved using various techniques, such as injection with retroviruses or adenoviruses, cationic liposome fusion, or naked DNA transfer. To determine the efficacy of these techniques for in vivo intracorporal cavernosal gene transfer, the plasmid pCMVβ was injected into the CC tissue of nine rats, in the forms of naked DNA (n=3), an incorporation of cationic liposomes (n=3), and a recombinant adenovirus containing the LacZ cDNA coding for β-galactosidase (n=3) (see Table 1). All three techniques of gene transfer produced positive results; however, adenoviral-mediated gene transfer was the most effective, as evidenced on the whole-tissue level by the conversion of the chromogenic substrate, X-Gal (5-bromo-4-chloro-3-indolyl-β-D-galactoside), into its blue breakdown product, as a result of β-galactosidase activity.

Naked DNA. To determine the relative number and histologic type of cells expressing β-galactosidase, 100 μg of pCMVβ plasmid (Clonetech, Calif.) (containing the LacZ gene under the control of the CMV promoter) in 200 μl of phosphate-buffered saline (containing 20% sucrose) were injected into the corpus cavernosum of 3-month-old Fischer rats (under anesthesia). Thirty days later, CCs from injected and control rats were excised, and then stained for β-galactosidase activity. β-galactosidase activity was evident in a significant number of the smooth muscle cells, thirty days after DNA injection.

Liposomes. Five μg of pCMVβ plasmid in 100 μl of PBS were mixed with 100 μl of Lipofectin reagent (Gibco). The resultant liposome complexes (200 μl) were injected into the corpus cavernosum of 3-month-old Fischer rats (under anesthesia). Ten days later, CC tissue was resected and stained for β-galactosidase activity.

Adenovirus vector. Two hundred μl of adenovirus vector (>$10^{10}$ pfu/ml) containing the LacZ cDNA were obtained from Dr. Roy Chowdhury (AECOM gene therapy core), and injected into the corpus cavernosum 3-month-old Fischer rats (under anesthesia). Three days later, CC tissue was resected and stained for β-galactosidase activity.

Microinjection of vectors/plasmids. Animals were anesthetized by intraperitoneal injection of sodium pentobarbital (35 mg/kg). An incision was made through the perineum, the corpus spongiosum was identified, and a window was made in the corpus spongiosum for identification of the corpus cavernosum. All microinjections consisted of a single bolus injection into the corporal tissue, made using an insulin syringe. The final volume of all microinjections was 200 μl.

4. Staining for β-galactosidase activity

CC tissue was excised from rats at various times after injection, fixed with 4% paraformaldehyde/0.1% glutaraldehyde for 3 hours, then stained with X-Gal for 15 hrs at 37° C. (Vitadello, et al., *Human Gene Therapy*, 5:11–18, 1994).

5. Gene transfer of LacZ into smooth muscle cells of the rat corpus cavernosum in vivo - Group B Transfer of LacZ DNA (coding for β-galactosidase) into rat corporal smooth muscle cells in vivo was accomplished by injecting the plasmid pCMVβ, as naked DNA, into the corporal tissue of 10-week-old Sprague-Dawley rats. The corporal tissue was obtained from groups of three animals at each of the four time points, ranging from 2–11 weeks post-injection (see Table 1 for details). An equivalent number of uninjected control animals, at each time point post-injection, was run in parallel. For these studies, 100 μg of pCMVβ plasmid were dissolved in 200 μl of PBS (containing 20% sucrose) and injected into the corpus cavernosum of 10-week-old Sprague-Dawley rats (under anesthesia). Two to eleven weeks later, the corporal tissue from injected and control rats was excised, fixed with 4% paraformaldehyde/0.1% glutaraldehyde for 3 hours, reacted with X-Gal for 15 hrs at 37° C., paraffin-embedded, and sectioned. The efficacy of gene transfer was assessed on the whole-tissue level by the conversion of the chromogenic substrate, X-Gal (5-bromo-4-chloro-3-indolyl-β-D-galactoside), into its blue breakdown product, as a result of the activity of β-galactosidase.

6. Injection of cDNA coding for neuronal NOS or maxi-K channel protein - Groups C and D Either the human maxi-K channel cDNA (hSlo) or the neuronal NOS cDNA was inserted into the XhoI-XbaI cloning sites of the pcDNA3 vector. One hundred μg of each plasmid (either pcDNA/maxi-K or pcDNA/NOS), in 200 μl of phosphate-buffered saline (containing 20% sucrose), were injected into the CCs of anesthetized 9-month-old Sprague-Dawley rats. Control rats were either sham-operated, sham-operated with an intracorporal injection of 200 μl of PBS (containing 20% sucrose), or sham-operated with an intracorporal injection of 200 μl of PBS containing 20% sucrose and 100 μg of pcDNA-vector DNA. Basal and nerve-stimulated intracorporal pressures (ICPs) were measured between 2 weeks and 4 months after intracavernous injection. No significant differences were observed in ICPs within the time frame examined, and results from all animals within each group were pooled. Similarly, no significant differences were observed among the various controls, and all control data were pooled.

Figure 4:
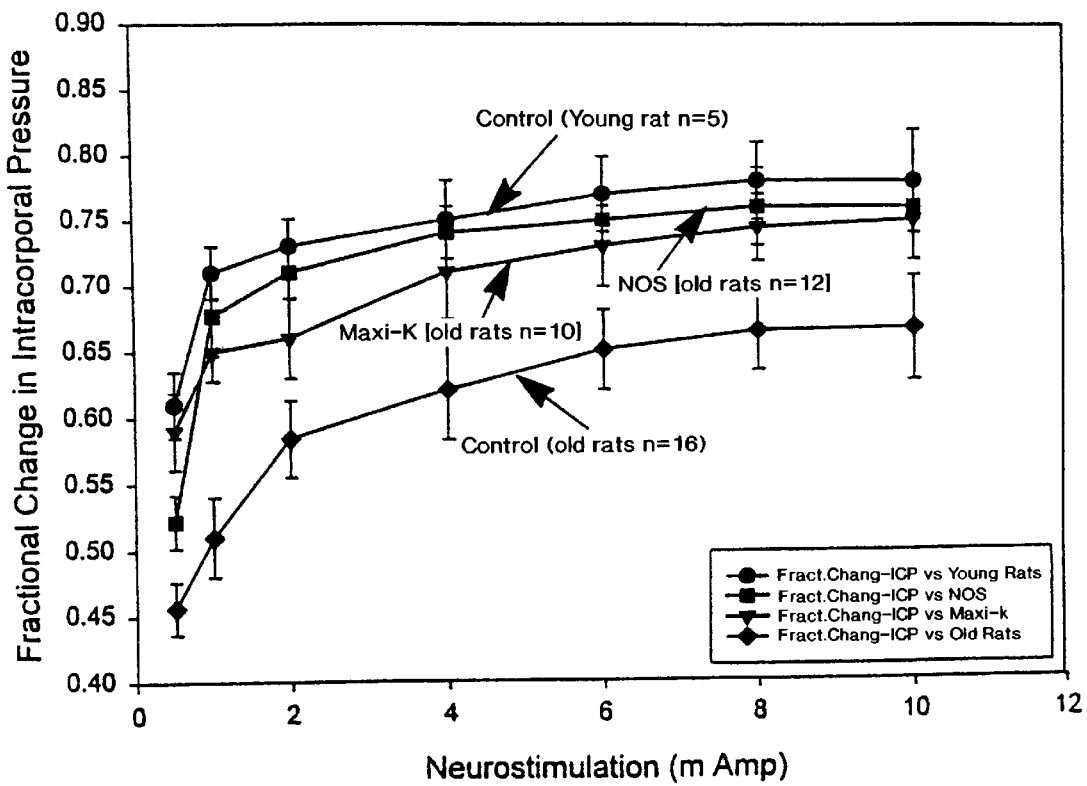
FIG. 4.
Figure 5:
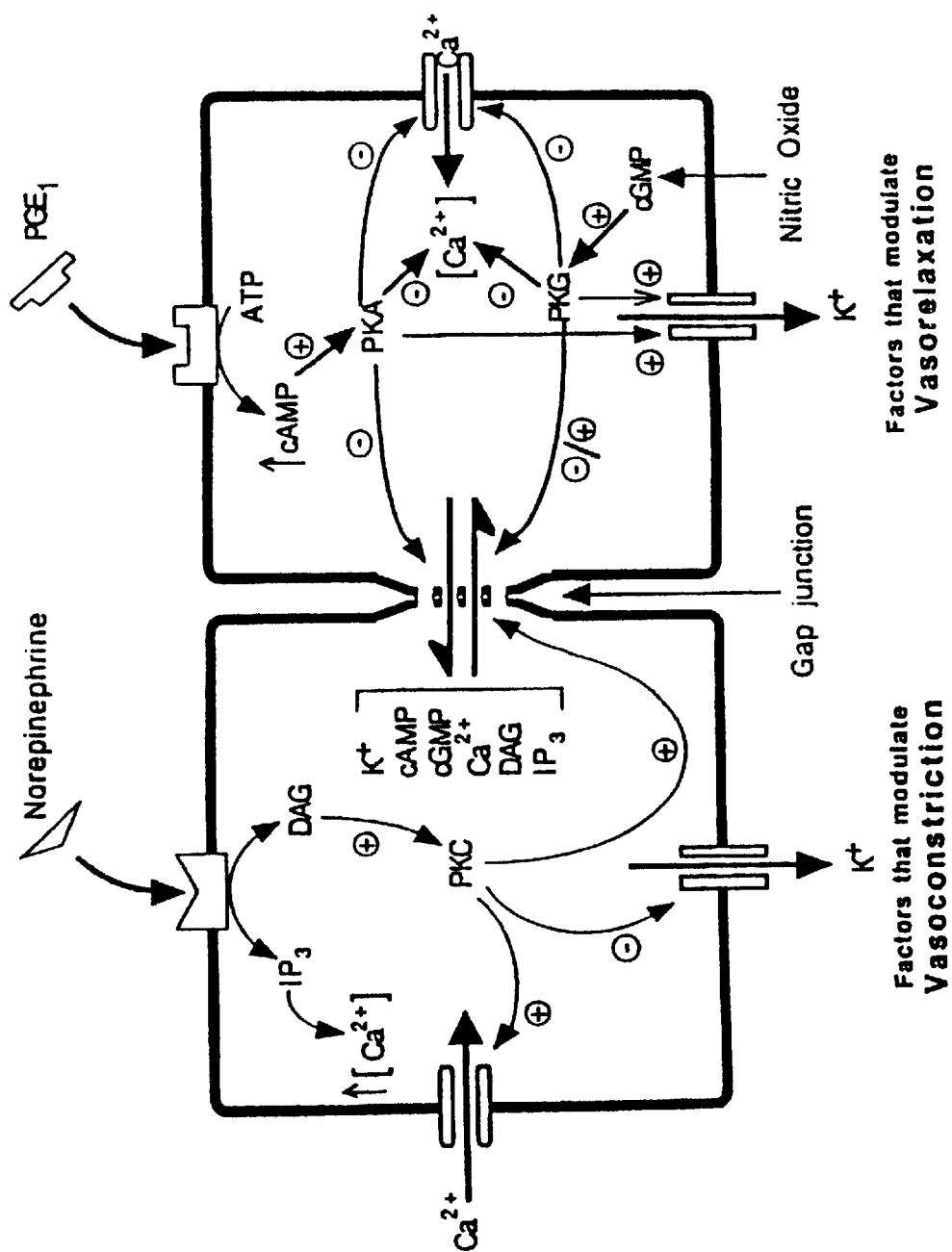
FIG. 5.
Figure 6:
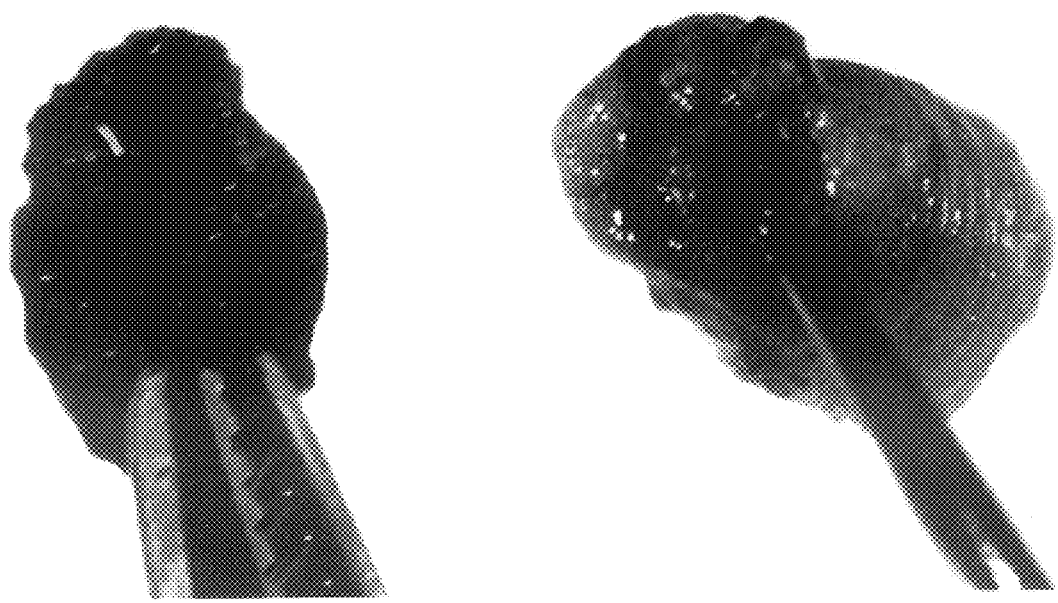
FIG. 6.

The data depicted in FIG. 4 and Table 2 indicate that the injection of either the NOS or maxi-K cDNA significantly increased both basal and nerve-stimulated ICPs. The mean basal fractional change in ICP increased from a control level of ~8 (cm of $H_2O$) to ~14 in NOS-injected rats, and to ~13 in maxi-K-injected rats. In a similar manner, the nerve-stimulated fractional change in ICP was approximately 30% higher in both NOS- and maxi-K-injected rats, over a range of 2–10 mA stimulation.

The age-matched control animals were considered to represent a homogeneous population, since statistical analysis revealed that there were no significant differences among these animals, 1–4 months after injection, with respect to the mean amplitude of the ICPs measured in response to all levels of current stimulation used in these studies. In addition, four retired breeders received an injection with pcDNA/hSlo DNA, as described below. Two months after this injection, the animals were sacrificed, and the corporal tissue was quickly excised and flash frozen in liquid nitrogen for RT-PCR and Northern analyses (without the performance of any physiological experiments in vivo). Five age-matched control animals, which were run in parallel, received injections of vehicle only.

7. Preparation of animals for in vivo erectile studies

Induction of anesthesia. The rats were anaesthetized by intraperitoneal injection (35 mg/kg) of sodium pentobarbital (Anpro Pharmaceuticals). Anesthesia was maintained during the course of the experimental protocol (2–3 hrs) by subsequent injection of pentobarbital (5–10 mg/kg) every 45–60 minutes, as required.

Figure 3:
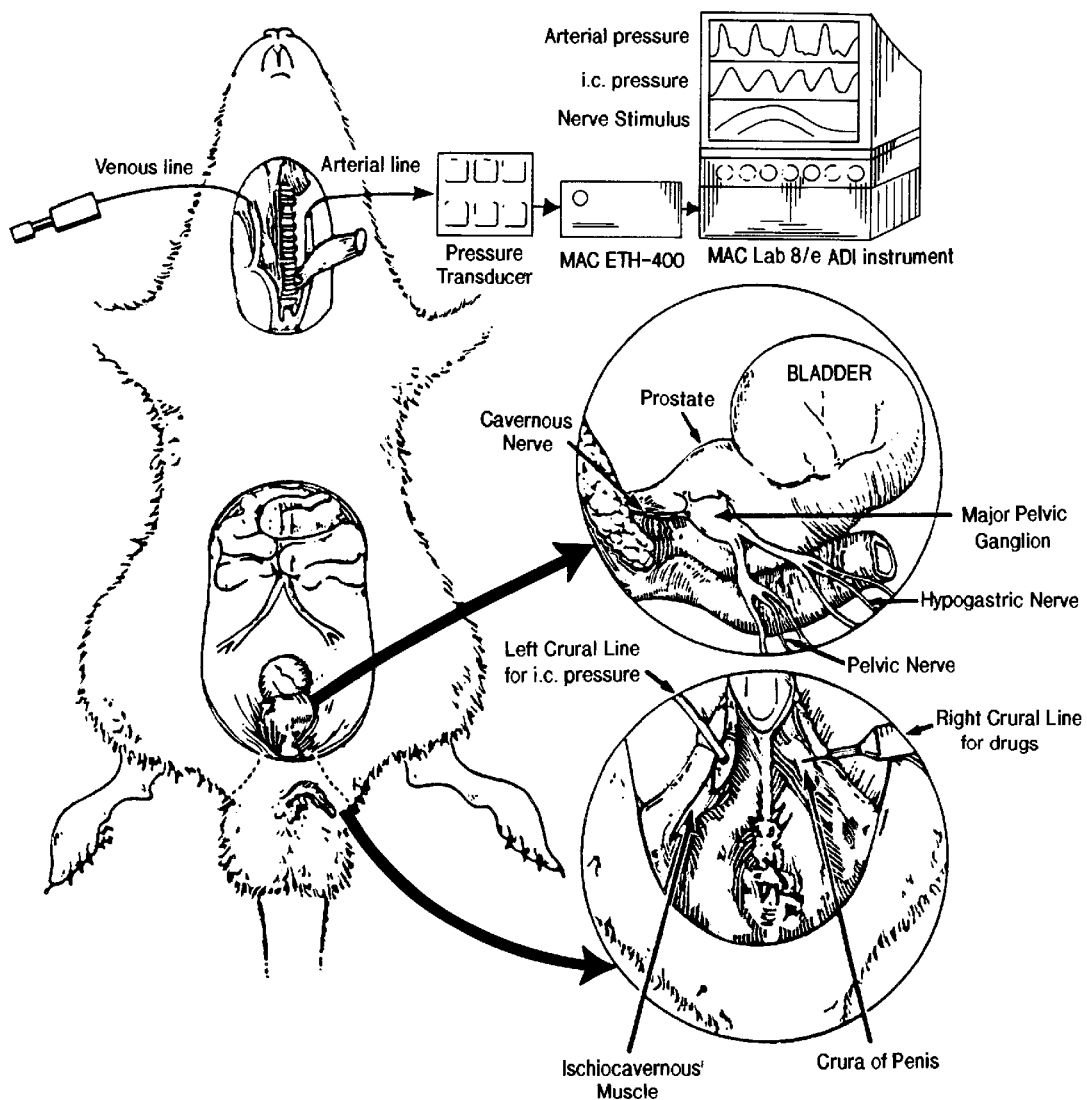
FIG. 3.

Surgical preparation and placement of pressure-monitoring cannulas. FIG. 3 illustrates the entire experimental procedure. Animals were anaesthetized, and placed in the supine position. The bladder and prostate were exposed through a midline abdominal incision. The arterial line in the left carotid artery was connected to a MacLab data acquisition board via a transducer and transducer amplifier, for continuous monitoring of blood pressure. A right external jugular venous line was utilized for intravenous fluid transfusion or blood sampling. The prostate was exposed by a lower midline incision. The cavernous nerve was seen on the posterolateral surface of the prostate, arising from the pelvic ganglion that is formed by the joining of the hypogastric and pelvic nerves. The two corpora were exposed by inguinoscrotal incisions on both sides, combined with degloving of the penis. A line was inserted into the right corpora for continuous monitoring of intracorporal pressure via the MacLab instrumentation. Yet another line was inserted into the left corpora, for intracavernous drug injection. Lastly, the nerve-stimulator probe was placed around the cavernous nerve for current stimulation. The inferior hypogastric plexus (i.e., the pelvic plexus or major pelvic ganglion), the pelvic nerve, and the cavernous nerve were identified posterolateral to the prostate, on both sides, and the stainless-steel bipolar wire electrodes were placed around these structures for electrical stimulation. Both crura of the penis were exposed by removing part of the overlying ischiocavernous muscle. In order to monitor intracorporal pressure (ICP), a 23-gauge cannula was filled with 250 U/ml of heparin solution, connected to PE-50 tubing (Intramedic, Becton Dickinson), and inserted into the right corpus cavernosum. The tubing was then fixed to the tunica with a 7-0 Dermalon suture, to ensure stability during measurement of ICP. Another 23-gauge cannula was connected to a 1-ml syringe, and inserted into the left corpus cavernosum for intracavernous drug injection. Systemic arterial blood pressure (BP) was monitored via a 25-gauge cannula placed into the carotid artery.

Both pressure lines, BP and ICP, were connected to a pressure transducer, which was, in turn, connected via a transducer amplifier (ETH 400 CB Sciences, Inc.) to a data acquisition board (MacLab/8e, ADI Instruments, MA). Real-time display and recording of pressure measurements were performed on a Macintosh computer (MacLab software v3.4). The pressure transducers and data acquisition board were calibrated in cm of $H_2O$.

Neurostimulation of cavernous nerve and recording of intracorporal pressure. Direct electrostimulation of the cavernous nerve was performed with a delicate stainless-steel bipolar hook electrode attached to the multijointed clamp. Each probe was 0.2 mm in diameter; the two poles were separated by 1 mm. Monophasic rectangular pulses were delivered by a signal generator (custom-made, with built-in constant current amplifier). Stimulation parameters were as follows: frequency, 20 Hz; pulse width, 0.22 msec; duration, 1 min. The current protocol involved the application of increasing current at the following intervals: 0.5, 1, 2, 4, 6, 8, and 10 mA. The changes in intracorporal pressure and systemic blood pressure were recorded at each level of neurostimulation.

8. Tissue procurement, fixation, and immunohistochemistry analysis

Tissue retrieval. Following completion of the neurostimulation experiments, the penises of both the gene therapy and age-matched control animals were harvested, and the distal end of each penis was marked with methylene blue to ensure the proper later identification of the distal and proximal ends. All penile tissue was immediately transferred to 4% paraformaldehyde in phosphate buffer (pH 7.4) for fixation for 4 hours at 20° C.; it was later cryoprotected in cold 30% sucrose in 0.1M PBS (pH 7.4), at 4° C. (overnight or longer), for immunostaining. Part of the penis of each animal was also frozen in liquid nitrogen and preserved at 80° C. for molecular biological studies. The penile tissue was sectioned on a cryostat at 14 $\mu$M; the sections were dried onto slides and paraffin-embedded. The slides were stored at $-20°$ C. until they were stained - usually within 2–4 weeks.

Histology. Histological examination of the sections was performed to confirm the identification of nerves and smooth muscles. Serial slide-mounted sections were fixed in 10% formalin, and stained with hematoxylin and eosin. All slide-preparation specimens were viewed with a Zeiss microscope.

Nitric oxide synthase immunohistochemistry. Slide-mounted tissue sections were deparaffinized with xylene, rehydrated in graded alcohols, and blocked for endogenous peroxidase activity with 3% hydrogen peroxide. Nonspecific binding of antibodies to the specimens was blocked by incubation with 1.5% normal goat serum in phosphate-buffered saline (PBS) for 30 minutes at room temperature. The slides were then drained and incubated with primary antibody, at room temperature, for one hour. The antibody was a rabbit polyclonal antibody directed against brain NOS (Transduction Laboratories, Lexington, Ky.). An antibody concentration of 1.0 $\mu$g/ml was found to be optimal for immunostaining. Antigen binding was detected by the avidin-biotin immunoperoxidase method, using the VectaStain Elite ABC kit. The color reaction was developed with diaminobenzidine that was activated with hydrogen peroxide (diaminobenzidine as the chromogen), and then counterstained with hematoxylin solution. Staining was not evident in the negative control, which substituted PBS for primary antibody, thereby providing support for the specificity of primary antibody used in the experiment.

Statistical analyses. All statistical analyses were performed using the Stat-View 4.5 software (Abacus Concepts, Berkeley, Calif.). Either a Two-Way analysis of variance (ANOVA) with post-hoc multiple comparisons (Tukey), or a two-tailed student-t test for unrelated samples, was utilized, as appropriate, for comparison of group means for parameters of interest among gene therapy (i.e., maxi-K transfected) rats, age-matched control rats, and young control rats. All differences were considered significant at $p<0.05$. Unless otherwise stated, all data will be expressed as the mean ($\pm$S.E.M.).

Construction of stimulus-response curves. Stimulus-response curves were generated to illustrate the effects of neurostimulation on intracorporal pressure by expressing the change in intracorporal pressure as a fraction of the mean systemic blood pressure (expressed in ICP/BP), then plotting this fraction as a function of the magnitude of neurostimulation (for 1, 2, 4, 6, 8, and 10 mA). All data were plotted using Sigma Plot software for Macintosh computers (Sigma Plot Mac v5.0, Jandel Scientific, San Rafael, Calif.).

9. Detecting expression of recombinant $K_{Ca}$

RNA preparation. Total RNA was extracted from frozen tissue using the TRIzol method. Briefly, tissue was homogenized in TRIzol reagent by a Polytron homogenizer (Brinkman, N.Y.) for about 30 seconds. The tissue lysate was then transferred to a polypropylene, 10×1.8 $cm^2$, round-bottom tube (Falcon, Becton Dickinson, N.J.), and incubated for 5 minutes at room temperature. Chloroform was then added, and the solution was centrifuged at 12,000 ×g for 15 minutes at 4° C. RNA in the aqueous phase was extracted from the TRIzol-and-chloroform mixture, and was then precipitated from the aqueous phase by mixing with isopropyl alcohol and centrifuging at 12,000×g for 10 minutes at 4° C. RNA was stored in 0.08M sodium acetate and 70% ethanol.

Northern blot analysis. Twenty $\mu$g of total RNA from each tissue sample was electrophoresed in 1% agarose containing 2.2M formaldehyde, then transferred onto nylon membranes by capillary transblotting. The positions of 28s and 18s ribosomal RNA bands on the ethidium-stained gels were observed under ultraviolet illumination before transblotting. RNA was fixed to the filter by heating for 2 hours at 80° C. The hSlo cDNA was cut from the Xhol and Xbal sites of pcDNA, purified on an agarose gel, labeled with random primer biotin using the NEBlot Phototype Kit (New England Biolabs), then used as cDNA probes for Northern blots. Hybridization was carried out in Rapid-hyb buffer (Amersham, Arlington Heights, Ind.) at 68° C. for 2 hours. Filters were washed two times in 2.5X SSC and 0.1% SDS, at room temperature, then washed two times in 1X SSC at 68° C. for 20 minutes, and three times in 0.1% SDS at 68° C. for 20 minutes. Following the washings, the membranes underwent detection steps using streptavidin and biotin alkaline phosphatase with CDP-Star substrate, according to the manufacturer's instructions (New England Biolabs). After incubation with CDP-Star substrate, the membranes were removed and exposed to the Hyperfilm (Amersham), in an intensifying screen, for at least 15 minutes. The film was developed with time adjustments, and the bands were analyzed.

RT-PCR. To further confirm and detect expression of the recombinant $K_{Ca}$, two distinct PCR strategies were used: (1) with primers specific to the plasmid sequences (T7 and SP6 promoters); and (2) with primers specific for the 5'-untranslated region (see below). With respect to the latter strategy, oligonucleotide primers for PCR amplification of the 5'-untranslated region (approximately 0.14 kb) were 5'-GCCGCCACCATTTGCCAT-3' (a 3' primer, coding for the first six amino acids of $K_{Ca}$) and 5'-CCCTATAGTGAGTCGTATTA-3' (a 5' primer, specific to the T7 promoter). With respect to the former strategy, oligonucleotide primers for PCR amplification of the full $K_{Ca}$ insert (approximately 4.2 kb) were the T7 promoter region (see above) and the SP6 promoter region (5'-CTAGCATTTAGGTGACACTATAG-3'). The primers for an endogenous $K_{Ca}$ region (bases 909–1074; 5'-GCTCTCCATATTTATCAGCAC-3' and 5'-AACATCCCCATAACCAAC-3') were used as controls.

The RT-PCR was performed using the Superscript One-Step RT-PCR System (Gibco BRL, Grand Island, N.Y.) with a final volume of 50 µl. The RT-PCR mixture included a buffer containing 1 µg of total RNA, 1 µM of the sense and antisense oligonucleotide primers, 0.4 mM of each dNTP Superscript II RT/Taq Mix, 80 units of $RN_{ASE}OUT$ recombinant ribonuclease inhibitor (Gibco BRL), and an optimized concentration of $MgSO_4$, as per manufacturer's instructions. First-strand cDNA was performed at 45° C. for 30 minutes, and denatured at 94° C. for 5 minutes. The PCR was performed with a cycle of annealing at 45° C. for 1 minute, extension at 72° C. for 1.5 minutes, and denaturing at 94° C. for 1 minute, for a total of 35 cycles with a final 10-minute extension step. For amplification of the full insert, one µl of eLONGase was added to the reaction mixture at 68° C. for 5 minutes of extension.

b) Gene Transfer of $K_{ATP}$ Through a Single Intracavernous Injection

1. Cloning of the Kir6.2 channel (Genbank Accession No. 50582) into the pVAX1 vector.

Total RNA was purified from corporal smooth muscle tissue by TRIzol reagent (Gibco) with glycogen as the carrier. The purified total RNA was subject to RT-PCR, according to the procedure described above. The primer set used for this RT-PCR was 5'-ggctcaagcttctgaggctggtattaagaagtg-3' (forward) and 5'-gcgcatctagatcctaaattgggttgggagg-3' (reverse). After RT-PCR, the cDNA fragment was TA cloned into pCRII, and then digested with Hind III and XbaI. The pVAX1 (Invitrogen), a 3.0-kb plasmid vector, was used as the expression vector. The pVAX1 was constructed by modifying the pcDNA3.1 vector to use kanamycin instead of ampicillin for selection, so as to avoid the potential pitfall of sensitivity to penicillin when injecting in humans. The unnecessary sequences for replication in *E. coli*, or for expression of the recombinant protein, were also removed. In addition, the pVAX1 was digested by Hind III and XbaI, then treated with alkaline phosphatase to reduce the background. The Kir6.2 cDNA was then ligated into the pVAX1. The Kir6.2 cDNA insert was oriented to follow the pCMVβ promoter. The cDNA insert was also sequenced to confirm the DNA sequences. The pVAX1/Kir6.2 construct was subsequently amplified and purified with the Giga prep (Qiagen), as before (Day, et al., FASEB J., 11:A328, 1997).

2. In vivo methods

For these experiments, retired breeder Sprague-Dawley rats (all 500 g) were transfected with Kir6.2/pcDNA naked DNA through a single intracavernous injection of 100 µg of Kir6.2/pcDNA in 200 µl of PBS, using procedures similar to those described above.

II. Bladder Dysfunction Gene Therapy Experiments a) Injection of LacZ DNA

LacZ DNA was prepared as described above. Briefly, transfer of LacZ DNA (coding for β-galactosidase) into rat bladder smooth muscle was accomplished by injecting the plasmid pCMVβ, as naked DNA, into the bladder. An abdominal incision was made in the pentobarbital-anesthetized rat (sodium pentobarbital, 35 mg/kg), and the bladder was exposed. Sixty-five µg of LacZ DNA, in 1 ml of buffer solution, were injected into the bladder using an insulin syringe. The needle opening was cauterized, the abdominal musculature was closed with sutures, and the skin was closed with surgical staples. Four days after injection, the animal was sacrificed by lethal injection. The bladder was quickly excised, placed in a 4% paraformaldehyde solution (for 4 hours), then transferred to the chromogenic solution (as described above). The bladder was then immediately placed in an incubator at 37° C. Fourteen hours later, the bladder tissue was removed from the incubator and photographed.

b) Gene Transfer of Maxi-K Using a Recombinant Vector

In the following experiments, 100 mg of hSlo/pcDNA was administered to female Sprague-Dawley rats in an effort to investigate the ability of maxi-K to ameliorate the bladder hyperactivity associated with 6 weeks of partial urethral obstruction (PUO) in the rats.

1. The rat model of bladder instability/incontinence

Bladder instability in the rat is reliably produced by narrowing the diameter of the urethra in the female rat, thereby creating an outflow obstruction. It has been documented that 6 weeks of such an obstruction will produce the optimal level of bladder instability, i.e., increased detrusor contractility in the absence of bladder decompensation and other systemic signs of morbidity and mortality (Malmgren, et al., J. Urol., 137:1291–94, 1987).

2. Surgical procedures to produce partial urethral obstruction and bladder outflow obstruction Female rats (Sprague-Dawley, 200–250 g) were utilized in these bladder experiments. The method used for producing the requisite urethral restriction was identical to that previously described (Malmgren, et al., J. Urol., 137:1291–94, 1987). Briefly, anesthesia was induced by the intraperitoneal injection (35 mg/kg) of sodium pentobarbital (Anpro Pharmaceuticals). Anesthesia was maintained during the course of the experimental protocol (<1 hr) as necessary, as judged by the presence of the toe-pinch reflex or the occurrence of appropriate alterations in respiratory rate. Following the course of the experimental protocol, anesthesia was maintained by subsequent injection of pentobarbital (5–10 mg/kg) every 45–60 minutes, as required.

Method of partial urethral obstruction. After anesthetic induction through intraperitoneal injection of sodium pentobarbital (35 mg/kg), the ventral abdominal wall and perineum of the rat were shaved with an electric shaver and cleaned with betadine. A lower midline abdominal incision was made, and the bladder and the proximal urethra were identified. A plastic rod with a 1-mm outer diameter was placed below the urethra, and a silk ligature was tied/placed around the urethra. After the ligature was secured, the externally-dwelling plastic rod was removed, and the animals were allowed to recover through the usage of systemic analgesic buprenorphine (0.02 mg/kg) and a warm lamp.

Method of catheterization. A second surgical procedure was performed on rats 6 weeks after the first surgery. The method utilized was again identical to that previously described (Malmgren, et al., J. Urol., 142:1134–38, 1989). The animal was anesthetized, as described for all other surgical procedures. The ventral abdominal wall and perineum were shaved with an electric shaver, and cleaned with betadine. A lower midline incision was made through the perineum, and the bladder and the proximal urethra were identified. A small incision was made in the bladder wall, and a PE catheter with a cuff was inserted into the bladder, with a top suture around the catheter. The bladder incision was closed with the suture. This chronic indwelling catheter was then tunneled in the subcutaneous space, and exited through an orifice made in the back of the animal. In order to prevent infections, the rats received subcutaneous injections of sulfadoxin (24 mg/kg) and trimethoprim (4.8 mg/kg), as previously described (Malmgren, et al., J. Urol., 142:1134–38, 1989). The abdominal incision was then sutured closed, and the free end of the catheter was sealed. Cystometrical analyses were performed two days after the surgery, as this has been shown to be an optimal period for recovery and investigation. At the conclusion of the experiment, all series-1 animals were sacrificed via deep intraperitoneal injection of pentobarbital.

3. In vivo cystometric analyses

Cystometric evaluation of bladder function was performed according to a previously-published procedure (Malmgren et al., 1989). Briefly, the bladder catheter was connected to a two-way valve that was, in turn, connected to a pressure transducer as well as an infusion pump. The pressure transducer was then connected via a transducer amplifier (ETH 400 CB Sciences, Inc.) to a data acquisition board (MacLab/8e, ADI instruments, MA). Real-time display and recording of pressure measurements was performed on a Macintosh computer (MacLab software v3.4, ADI instruments, MA). The pressure transducers and data acquisition board were calibrated in cm of $H_2O$, prior to each experiment.

Essentially, the cystometry evaluated the micturition reflex in control and hypertrophic animals, and in genetherapy animals, at various time points, post-urethralrestriction. The rate of infusion was set on a programmable Harvard Infusion pump (model PHD 2000), and was based on previously-published work. This was found to be sufficient for the inventors' purposes. In order to obtain an approximately-equal number of micturitions in the control and hypertrophic groups (both treated and untreated with gene therapy) during the cystometry period, the rate of infusion was 10 and 20 ml/hr, respectively. The saline infusion was started, and, following the first micturition, three additional reproducible micturition cycles, each corresponding to a 20-minute period, were recorded on each animal prior to sacrifice. All experiments were performed in a metabolic cage, to allow determination of the micturition volume.

At the conclusion of the experiment, all animals were sacrificed using deep intraperitoneal injection of pentobarbital. Bladder function was then evaluated according to the following urodynamic criteria:

1. bladder capacity: volume of infused saline at micturition;
2. basal pressure: the lowest bladder pressure recorded during cystometry;
3. threshold pressure: bladder pressure immediately prior to micturition;
4. micturition pressure: peak bladder pressure during micturition;
5. micturition volume: the volume of urine discharged during micturition;
6. residual volume: volume of infused saline minus the micturition volume;
7 spontaneous activity: mean amplitude and frequency of bladder pressure fluctuations; and
8. bladder compliance: bladder capacity/(threshold pressure minus basal pressure).

In addition, the mean intermicturition pressure (MIP) was derived as follows. Firstly, the average bladder pressure recorded between micturitions (i.e., the intermicturition pressure) was obtained from each animal for the entire intermicturition period. The measured basal pressure was then subtracted from the intermicturition pressure for the same animal, in order to obtain a value for the MIP. As such, the MIP serves as a proximal index of the fluctuations in bladder pressure, if any, between the recorded micturition reflexes.

B. Results and Discussion

I. Erectile Dysfunction Gene Therapy Experiments a) Gene Transfer of Maxi-K Using a Recombinant Vector 1. Roles of potassium channels and nitric oxide in regulating corporal smooth muscle function Evidence that alterations in potassium-channel function can increase "sensitivity" to relaxation. Recent studies by the inventors have indicated that hyperpolarization of corporal smooth muscle cells via activation of $K^+$ channels represents an important mechanism for controlling corporal smooth muscle tone (Holmquist, et al., J. Urol., 144:146, 1990; Christ, et al., *Journal of Andrology*, 14(5):319–28, 1993; Fan, et al., J. Urol., 153:818, 1995; and Christ, G. J., *Urological Clinics of North America*, 22(4):727–45, 1995). This observation reflects the fact that sustained contraction of human corporal smooth muscle, which is characteristic of flaccidity (the condition which is prevalent in the vast majority of cases), is largely dependent on continuous transmembrane $Ca^{2+}$ flux through voltage-gated $Ca^{2+}$ channels.

The activity of the voltage-dependent $Ca^{2+}$ channels in corporal smooth muscle cells is, in turn, closely modulated by hyperpolarizing currents, initiated and carried mainly by prostaglandin $E_1$ ($PGE_1$). Among the subtypes of $K^+$ channels, the ~180 pS $Ca^{2+}$-sensitive (maxi-K) channel is one of the most prominent in corporal smooth muscle cells (Fan, et al., J. Urol., 153:818, 1995). Membrane hyperpolarization of corporal smooth muscle cells, following activation of $K^+$ channels, can be accomplished by both receptor-mediated (e.g., PGE or NO) and nonreceptor-mediated (e.g., NO or cGMP) stimuli, derived from neuronal as well as endothelial sources. These data are summarized in Table 4.

The putative mechanism of action is described as follows: release of an endogenous corporal vasorelaxant(s) (e.g., NO) is thought to either directly activate the $K^+$ channel, or regulate $K^+$-channel activity following a series of events involving activation of soluble guanylate cyclase, an increase in intracellular cGMP levels, activation of protein kinase G, and phosphorylation of cellular proteins, including nonfunctional ion channels such as K$^+$ and Ca$^{2+}$ channels. Increased kinase activity (either A or G) has opposite effects on Ca$^{2+}$ and K$^+$ channels, causing decreased activity in the former and increased activity in the latter. Thus, an elevation in intracellular NO and/or CGMP levels can result in both activation of K$^+$ channels and inhibition of Ca$^{2+}$ channels. The algebraic sum of these two opposing effects significantly diminishes transmembrane Ca$^{2+}$ flux, resulting in diminished corporal smooth muscle tone, and, therefore, corporal smooth-muscle relaxation.

Since the activity of the maxi-K channel appears to be modulated by all of the physiologically-relevant endogenous regulators of corporal smooth muscle tone (FIG. 2), including PGE (Zhao, et al., J. Urol., 154:1571–79, 1995; Zhang, et al., *J. Urol.*, 155:678A, 1996; and Zhao, et al., *J. Urol.*, 155:678A, 1996) and NO, the maxi-K channel is clearly an important final common mediator of the degree of corporal smooth muscle tone. The inventors have preliminary evidence, consistent with this hypothesis, suggesting that altered regulation/function of this channel may represent an important feature of organic erectile dysfunction per se in human corporal smooth muscle (Fan, et al., *J. Urol.*, 153:818, 1995; Christ, G. J., *Urologic Clinics of North America*, 22(4):727–45, 1995; and Christ, et al., *J. Urol.*, 155:620A, 1996). For all of these reasons, the inventors feel that the relatively-stable transfection of corporal smooth muscle cells with the human smooth muscle maxi-K channel cDNA represents an important and attractive strategy for modulating erectile capacity.

Evidence that increases in the amount of nitric oxide can increase the "driving force" for relaxation of corporal smooth muscle. An abundance of recent experimental evidence documents the important role played by NO in arterial and corporal smooth-muscle relaxation and, consequently, in penile erection (Burnett, et al., *Science,* 257(5068):401–403, 1992; Trigo-Rocha, et al., *J. of Physiology,* 264(2):H419–22, 1993; Argiolas, et al., *Neuropharmacology,* 33(11):1339–44, 1994; and Burnett, et al., *Biology of Reproduction,* 52(3):485–89, 1995). For example, electrical stimulation of both human (Saenz de Tejada, et al., *New England Journal of Medicine,* 320(16):1025–30, 1989) and rabbit (Ignarro, et al., *Biochem. Biophys. Res. Commun.,* 170:843–50, 1990) corporal cavernosal muscle strips results in smooth-muscle relaxation. These responses are thought to be mediated by release of NO. Consistent with this supposition, these relaxation responses can be inhibited by nitroglycerine-substituted analogues of L-arginine, which block NO formation (Ignarro, et al., *Biochem. Biophys. Res. Commun.,* 170:843–850, 1990; Holmquist, et al., *Acta Physiol. Scand.,* 141:441–42, 1991; and Kim, et al., *J. Clin. Invest.,* 88:112–18, 1991). Furthermore, the relaxation of both human and rabbit corporal smooth muscle can be induced through compounds that release NO (Ignarro, et al., *Biochem. Biophys. Res. Commun.,* 170:843–50, 1990; Rajfer, et al., *New England Journal of Medicine,* 326:90–94, 1992; and Christ, et al., *Urological Clinics of North America,* 22(4):727–45, 1995). The importance of the NO-dependent pathway for relaxation of human corporal smooth muscle has also been documented (Bush, et al., *J. Urol.,* 147:1650–55, 1992; Trigo-Rocha, et al., *Neurology & Urodynamics,* 13(1):71–80, 1994; and Christ, et al., *Canadian Journal of Physiology and Pharmacology,* 73:714–26, 1995).

Nitric oxide is produced by the enzyme nitric oxide synthase (NOS), as a product of the enzymatic conversion of L-arginine to L-citrulline. Nitric oxide is produced in endothelial cells, upon cholinergic stimulation or by euronal sources (e.g., released from NANC nerve terminals). With respect to he latter, NO is a novel neurotransmitter in that it is not stored in synaptic vesicles in nerve terminals, but is synthesized on demand. Biochemical and histochemical evidence in rabbit and rat penis suggests that the NOS isozyme which functions in penile erection belongs to the cNOS type (Burnett, et al., *Science,* 257(5068):401–403, 1992). A neural source for NOS in the rat penis was demonstrated by J. R. Keast (*Neurosciences Letter,* 143:69–73, 1992), where NOS was localized to the autonomic nerves of rat and human penis by immunohistochemistry with rat cNOS antibody, and by NADPH diaphorase histochemistry (Burnett, et al., *Science,* 257(5068):401–403, 1992; and Burnett, et al., *J. Urol.,* 150(1):73–76, 1993). The mechanism of action of NO is thought to be as follows: after production, NO (a highly lipophilic substance) quickly diffuses in three dimensions (Christ, et al., *Biophysical Journal,* 67:1335–44, 1994) into corporal smooth muscle cells, where it results in activation of soluble guanylate cyclase, which catalyzes the conversion of GTP to cGMP. The increase in cGMP activates protein kinase G (PKG), which, as illustrated in FIG. 2, leads to decreases in intracellular Ca$^{2+}$, producing corporal smooth-muscle relaxation (Moncada, S., *Acta Physiol. Scand.,* 145:201–27, 1992). As mentioned above, there is also recent evidence that, in at least some vascular smooth muscle cells, NO may directly interact with K$^+$ channels to elicit hyperpolarization and smooth-muscle relaxation.

In the flaccid state, NOS activity is thought to be minimal (Ignarro, et al., *Biochem. Biophys. Res. Commun.,* 170:843–50, 1990; Rajfer, et al., *New England Journal of Medicine,* 326:90–94, 1992; Azadozi, et al., *J. Urol.* 147(1):220–25, 1992; Brock, et al., *Urology,* 42(3):412–17, 1993; Hellstrom, et al., *J. Urol.,* 151(6):1723–27, 1994; Pickard, et al., *British Journal of Urology,* 75(4):516–22, 1995; Carrier, et al., *J. Urol.,* 153(5):1722–27, 1995; Garban, et al., *American Journal of Physiology, H*467–H475, 1995; and Burnett, et al., *Biology of Reproduction,* 52(3) :485–89, 1995). The intensity of the histochemical detection of NADPH diaphorase in cavernosal tissue has been shown to decrease in patients with cavernosal nerve injury, implying decreased NOS activity (Brock, et al., *Urology,* 42(3):412–17, 1993). Furthermore, it has been suggested that the impaired relaxation responses to electric field stimulation, elicited by the cavernosal nerves of diabetic men, may also be due to decreased NOS production (Saenz de Tejada, I., *New England Journal of Medicine,* 320(16):1025–30, 1989; Taub, et al., *Urology,* 42:698, 1993; Christ, G. J., *Urologic Clinics of North America,* 22(4):727–45, 1995; and Vernet, et aL, *Endocrinology,* 136:5709–17, 1995). Thus, the introduction of a constitutively-expressed cDNA for NOS might be expected to result in corporal smooth-muscle relaxation and greater resting and nerve-stimulated pressure responses. As described below, the cDNA for neuronal NOS has been inserted into the corpora cavernosa of rats, and a statistically-significant and physiologically-relevant alteration was observed in the intracorporal pressure response to electrical stimulation of the cavernous nerve (see Table 2 below).

TABLE 2

Intracorporal pressure (ICP) response
following nerve stimulation in NOS group and control group

| | | Cavernous Nerve Stimulation | | | | | | |
|---|---|---|---|---|---|---|---|---|
| | BCP♣ (Basal) | ICP♦ 0.5 mA♥ M ± SEM♠ | ICP 1 mA M ± SEM | ICP 2 mA M ± SEM | ICP 4 mA M ± SEM | ICP 6 mA M ± SEM | ICP 8 mA M ± SEM | ICP 10 mA M ± SEM |
| NOS gene therapy (n = 12) | 14.62 ± .64 | 60.02 ± 5.9 | 102.50 ± 3.89 | 110.49 ± 4.65 | 113.93 ± 2.17 | 117.72 ± 2.80 | 121.26 ± 3.26 | 129.03 ± 5.4 |
| Age-Matched Control (received vehicle only) (n = 8) | 8.1 ± .37 | 45.81 ± 3.63 | 75.242 ± 3.59 | 83.93 ± 3.23 | 83.59 ± 4.52 | 85.67 ± 3.75 | 87.94 ± 4.45 | 92.23 ± 3.62 |
| P value | .0001 | .0085 | .0001 | .0001 | .0001 | .0001 | .0001 | .0003 |

*cavernous-nerve stimulation performed on both sides (observation = 2 × the # of rats)
♣BCP = basal corporal pressure in cm of $H_2O$ before neurostimulation
♦ICP = intracorporal pressure in cm of $H_2O$
♥mA = milliAmperes of stimulus to the nerve
♠M ± SEM = mean and standard error of the mean 2. Results of in vitro experiments involving maxi-K channels Evidence that $K^+$ channels modulate corporal smooth-muscle relaxation. Evidence from both cellular and isolated-tissue studies documents the important role of the maxi-K channel in mediating NTG- and $PGE_1$-induced relaxation responses in the human corpora.

NTG and maxi-K. In addition to the aforementioned effects on PE—induced contractile responses, selective blockade of the maxi-K channel with 1 mM tetraethylammonium (TEA) also results in significant attenuation of the NTG-induced relaxation response (100 nM), as illustrated by the representative example in FIG. 1. Studies on five other corporal tissue strips revealed that the mean ±S.E.M. percent relaxation response elicited by 100 nM nitroglycerine (NTG) was 20.3%±3.2%. This value can be compared with the expected value of 50.1%, as determined in another recent publication. This more recent finding documents that activation of the maxi-K channel is also likely to be an important component of the NTG—induced relaxation response. Consistent with this hypothesis, preliminary patch-clamp studies (i.e., attached patch recording mode) on cultured corporal smooth muscle cells, albeit with much greater NTG concentrations (100 μM), demonstrated an NTG-induced increase in maxi-K channel activity in cultured corporal smooth muscle.

$PGE_1$ and maxi-K. Recent electrophysiological studies utilizing all four recording modes documented that prostaglandin $E_1$ ($PGE_1$) causes a concentration-dependent increase in the activity of the maxi-K channel over the same concentration range as the inventors observed in cultured cells, and relaxation of precontracted isolated human corporal smooth muscle strips (Zhang, et al., J. Urol., 155:678A, 1996). In addition, this increase in maxi-K channel activity is correlated with significant alterations in the induced intracellular calcium transient seen in fura-2-loaded cultured corporal smooth muscle cells. Specifically, preincubation of cultured human corporal smooth muscle cells with 500 nM $PGE_1$ resulted in a significant (≈40%) decrease in the peak amplitude of the ET-1-induced (50 nM) calcium transient above baseline (i.e., ≈70 nM) from a control value of 161.5±19.5 nM to 102.6±9.5 nM (Zhao, et al., J. Urol, 155:678A, 1996). This decrease is indistinguishable from the decrease seen in the absence of extracellular $Ca^{2+}$ (in 2 mM EGTA), or when cells are preincubated with either nifedipine (Zhao and Christ, J. Urol., 154:1571–79, 1995) or verapamil, both of which are blockers of the L-type voltage-dependent calcium channel.

Finally, it is shown (Table 3) that transfection of cultured human corporal smooth muscle cells with human smooth muscle maxi-K cDNA (hSlo) results in a significant decrease (≈25%) in the mean resting intracellular calcium levels, as well as a decrease (≈45%) in the peak amplitude of the ET-1-induced intracellular calcium transient. While the physiological significance of the former observation is uncertain, the effects of transfection on the ET-1-induced intracellular calcium transient (Table 5) are remarkably similar to those seen in the presence of $PGE_1$, nifedipine, and verapamil, and in the absence of extracellular calcium.

TABLE 3

Summary of documented in vitro effects of the maxi-K channel on the physiology of corporal smooth muscle

| PE-induced contraction increased | Resting corporal smooth muscle tone increased | Resting intracellular calcium levels decreased | ET-1-induced calcium response decreased | Relaxation response decreased | Channel activity increased |
|---|---|---|---|---|---|
| YES (1 mM TEA) | YES (10–100 mM TEA) | YES transfection with | YES transfection with hSlo cDNA or | YES (1 mM TEA) | YES 100 μM NTG or 30 nM- |

TABLE 3-continued

Summary of documented in vitro effects of the maxi-K channel on the physiology of corporal smooth muscle

| PE-induced contraction increased | Resting corporal smooth muscle tone increased | Resting intracellular calcium levels decreased | ET-1-induced calcium response decreased | Relaxation response decreased | Channel activity increased |
|---|---|---|---|---|---|
| | (hSlo cDNA) | preincubation with PGE$_1$ (500 nM) | | | 30 μM PGE$_1$ |

Calcium flux and maxi-K channels. Taken together, the preceding data are totally consistent with the hypothesis that increased maxi-K channel activity, either following an increase in the number of maxi-K channels (presumably resulting from the transfection, although this has not yet been unequivocally established), or following cellular activation with, for example, PGE$_1$, is associated with cellular hyperpolarization, decreased transmembrane Ca$^{2+}$ flux through L-type voltage-dependent Ca$^{2+}$ channels, and a corresponding decrease in the peak amplitude of the ET-1-induced calcium transient. Moreover, the peak amplitude of the intracellular calcium transient, as measured in cultured corporal smooth muscle cells, accurately tracks the magnitude of the steady-state contractile response measured on isolated corporal tissue strips (Christ, et al., *J. Urol.*, 153:1998–2003, 1995). This provides compelling evidence that increased activity of the maxi-K channel modulates the magnitude of the corporal smooth muscle contractile response, at least in part, by altering transmembrane Ca$^{2+}$ flux. The maxi-K channel plays a dual role in modulating the magnitude of both contraction and relaxation. This dual role arises because maxi-K-induced inhibition of transmembrane Ca$^{2+}$ flux can occur following agonist (PE or ET-1)-induced increases in intracellular CA$^{2+}$, or following PGE$_1$ (presumably PKA)-induced or NTG (presumably PKG)-induced increases in phosphorylation of the maxi-K channel. Indeed, this is consistent with the literature in other vascular smooth muscle cell types (see Table 4).

TABLE 4

Effects of vasoactive compounds on ion-channel activity, membrane potential, and corporal smooth muscle tone

| Agonist | Channel Type Affected | Putative Mechanism | Effect on Smooth Muscle Tone |
|---|---|---|---|
| | Membrane Potential −30 mV (DEPOLARIZED, i.e., contracted) | | |
| ET-1 | L-type Ca$^{2+}$ increases | voltage or phosphorylation | increased tone |
| PE | K$_{Ca}$ increases | Ca$^{2+}$-sensitive | modulates increase in tone |
| KCl | K$_{ATP}$ increases | decreased ATP | modulates increase in tone |
| TEA | K$_{Ca}$ decreases | channel blockade | increased tone |
| Glibenclamide | K$_{ATP}$ decreases | channel blockade | increased tone |
| | ↑ −40 to −50 mV (RESTING POTENTIAL) ↓ | | |
| PGE$_1$ | K$_{Ca}$ increases | phosphorylation | decreased tone |
| NTG | L-type Ca$^{2+}$ | voltage or | decreased tone |

TABLE 4-continued

Effects of vasoactive compounds on ion-channel activity, membrane potential, and corporal smooth muscle tone

| Agonist | Channel Type Affected | Putative Mechanism | Effect on Smooth Muscle Tone |
|---|---|---|---|
| pinacidil | decreases K$_{ATP}$ increases | phosphorylation increased mean open time | decreased tone |
| | Membrane Potential −60 mV (HYPERPOLARIZED, i.e., relaxed) | | |

TABLE 5

Effect of transfection with hSlo cDNA on resting and ET-1-induced changes in Ca$_i$

| Control Cells (n = 17) | | TT Transfected Cells (n = 32) | |
|---|---|---|---|
| Resting Ca$_i$ | ET-1 (50 nM) | Resting Ca$_i$ | ET-1 (50 nM) |
| 74.7 ± 4.0 nM | 164.1 ± 17.8 nM | *56.7 ± 2.5 nM | *90.8 ± 6.6 nM |

*denotes a statistically-significant difference from control values
Ca$_i$ = intracellular calcium concentration
p < 0.001, student-t test for unpaired samples
The values given in Table 5 for the ET-1-induced increase represent the peak amplitudes of the intracellular calcium transient, as described in Zhao and Christ, J. Urol., 154:1571–79, 1995.

3. Results of in vivo gene therapy experiments to treat erectile dysfunction

Selection of rat model. The rat was selected for the gene therapy studies, as the rat penis has been shown to be histologically and pharmacologically similar to human penis (Lesson, et al., *Investigative Urology*, 3(2):144–45, 1965). Among many known models, the rat is excellent for the study of penile erection (Lesson, et al., *Investigative Urology*, 3(2):144–45, 1965); Quinlan, et aL, *J. Urol*, 141 (3):656–61, 1989; Chen, et al., *J. Urol.*, 147:1124–28, 1992; and Martinez-Pineiro, et al., *European Urology*, 25:62–70, 1994), as well as neurogenic and diabetic impotence (Rehman, et al., *Am. J. Physiol.*, 41:H1960–71, 1997).

Figure 7A:
FIGS. 7A and 7B set forth the results of an histological analysis of naked pCMVβ/LacZ gene transfer into rat corpora in vivo.

Transfection of pCMVβ/LacZ into rat corpora in vivo. Twelve rats were injected with pCMVβ/LacZ and followed for up to ≈11 weeks (75 days) post-injection; an equivalent number of age-matched control rats were run in parallel (see Table 1). Histological evaluation of corporal tissue excised from rats receiving an intracorporal injection of naked LacZ DNA revealed the presence of significant chromogenic material in 10 out of 12 animals. FIG. 7A shows a representative example of the presence of chromogenic material in the corpora of a rat, 60 days post-injection. It appears that incorporation of naked DNA is sustained, over this time period, in this tissue. Similarly, prolonged incorporation of gene transfer products has been reported in other vascular tissues.

Figure 9:
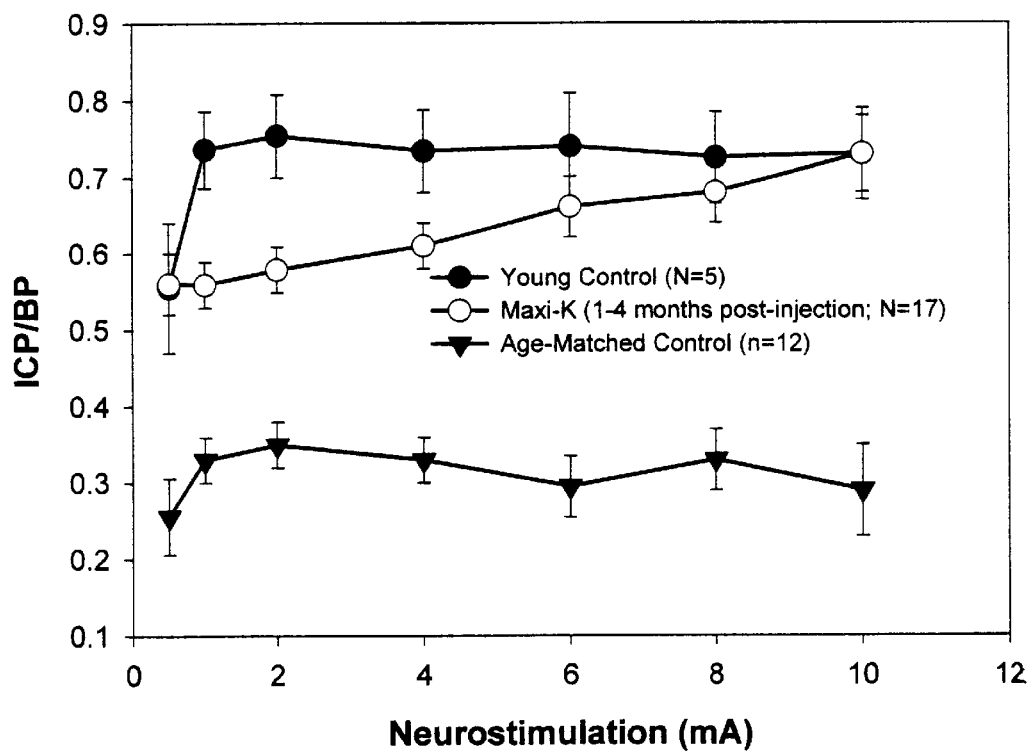
FIG. 9.

Injection of hSlo naked DNA into rat corpora in vivo. As a first test of the potential utility of modulating $K^+$ channel activity to treat erectile dysfunction, preliminary studies were conducted on a rat model in vivo. Briefly, it was found that injection into the rat corpora of naked cDNA encoding the human smooth muscle maxi-K channel (hSlo, obtained from Dr. Salkoff, Washington University) resulted in significant uptake and gene expression. This was documented by the fact that the nerve-stimulated intracorporal-pressure increases observed on 9-month-old Sprague-Dawley rats injected with maxi-K cDNA were significantly greater than the ICP responses seen in age-matched control, sham-operated animals (see FIG. 9 and Table 6). Moreover, the incorporation of hSlo (again, as judged by the significant elevation of ICP relative to control animals) remained stable for more than 3 months. These in vivo studies are entirely consistent with all of the in vitro observations made by the inventors, and, thus, further document the importance of $K^+$ channels in modulating corporal smooth muscle tone. Moreover, while it is recognized that there may be other subunits of the human smooth muscle maxi-K channel in human corporal tissue, these studies represent a reasonable starting point for evaluating the role of the maxi-K channel in erectile physiology.

Figure 8:
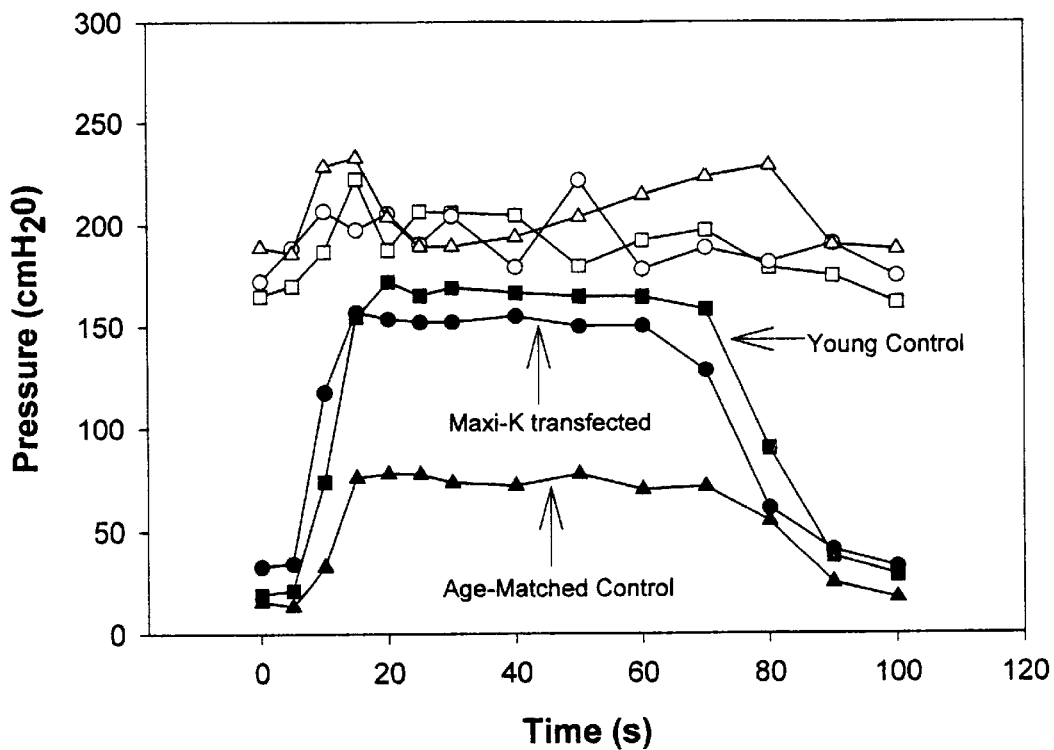
FIG. 8.

The effects on the ICP response in rats in vivo of current stimulation of the cavernous nerve were utilized to evaluate the potential physiological relevance of over-expression of the maxi-K channel following intracavernous injection of the pcDNA/hSlo DNA (see Materials and Methods). For these studies, the rats were divided into distinct treatment groups. All animals were examined using identical neuro-stimulation protocols, with the magnitude of current stimulation ranging from 0.5 mA to 10 mA. Representative responses to 2 mA-current stimulation in pcDNA/hSlo-transfected animals, age-matched control animals, and young control animals are illustrated in FIG. 8.

For statistical comparison of treatment effects, the mean amplitude of the ICP response at each level of current stimulation was expressed as a fraction of the mean arterial blood pressure (ICP/BP) during current stimulation. A Two-Way (ANOVA) analysis of variance revealed that there was a significant effect of treatment ($p<0.001$) on the mean ICP/BP, but no effect of current stimulation ($p>0.13$), and no treatment-current stimulation interaction ($p=0.26$). The mean response for all animals in each treatment group is graphically represented in FIG. 9, and the data are summarized in Table 6. Although post-hoc analysis documented a significant difference in the mean amplitude of the ICP response to all levels of current stimulation between the young control group and the maxi-K-transfected group ($p<0.05$), both groups had ICP responses that were significantly elevated over those of the age-matched control animals ($p<0.05$).

TABLE 6

Mean intracorporal pressure (ICP) and blood pressure (BP) measurements made during cavernous nerve stimulation

| Neurostim-ulation (mA) | Maxi-K-injected (N = 17) | | Age-Matched Control (N = 12) | | Young Control (N = 5) | |
| --- | --- | --- | --- | --- | --- | --- |
| | ICP ($cmH_2O$) | BP ($cmH_2O$) | ICP ($cmH_2O$) | BP ($cmH_2O$) | ICP ($cmH_2O$) | BP ($cmH_2O$) |
| 0.5 | 111 ± 7 (n = 6) | 198 ± 6 | 43 ± 11 (n = 5) | 178 ± 12 | 102 ± 16 (n = 5) | 183 ± 16 |
| 1.0 | 107 ± 7 (n = 16) | 192 ± 5 | 55 ± 5 (n = 12) | 178 ± 6 | 132 ± 10 (n = 5) | 180 ± 10 |
| 2.0 | 114 ± 11 (n = 16) | 198 ± 5 | 63 ± 5 (n = 12) | 177 ± 7 | 133 ± 10 (n = 5) | 180 ± 10 |
| 4.0 | 121 ± 7 (n = 15) | 196 ± 5 | 57 ± 5 (n = 12) | 177 ± 7 | 133 ± 10 (n = 5) | 186 ± 10 |
| 6.0 | 124 ± 5 (n = 11) | 190 ± 6 | 53 ± 6 (n = 9) | 180 ± 9 | 131 ± 13 (n = 3) | 181 ± 10 |
| 8.0 | 129 ± 5 (n = 8) | 191 ± 5 | 59 ± 7 (n = 9) | 181 ± 9 | 133 ± 11 (n = 4) | 184 ± 11 |
| 10.0 | 142 ± 6 (n = 7) | 195 ± 5 | 56 ± 13 (n = 4) | 191 ± 7 | 132 ± 11 (n = 4) | 180 ± 11 |

Resting and neurostimulation-induced ICP responses in maxi-K-transfected and sham-operated control rats. A One-Way (ANOVA) analysis of variance revealed that there was a significant difference in the resting ICPs of rats transfected with the pcDNA/hSlo DNA; however, there was no detectable difference in the mean resting ICP or mean arterial pressure values among the three treatment groups ($p>0.07$). The mean ±S.E.M. values for ICP and BP, respectively, for the pcDNA/hSlo-transfected rats (N=17) were 22.7±1.9 and 177.4±4.3 $cmH_2O$. These values were 14.9±3.3 and 177±4.5 $cmH_2O$, respectively, for the age-matched control animals (N=12), and 19.8±3.3 and 168.6±7.4 $cmH_2O$, respectively, for the young control animals (N=5).

Figure 10A:
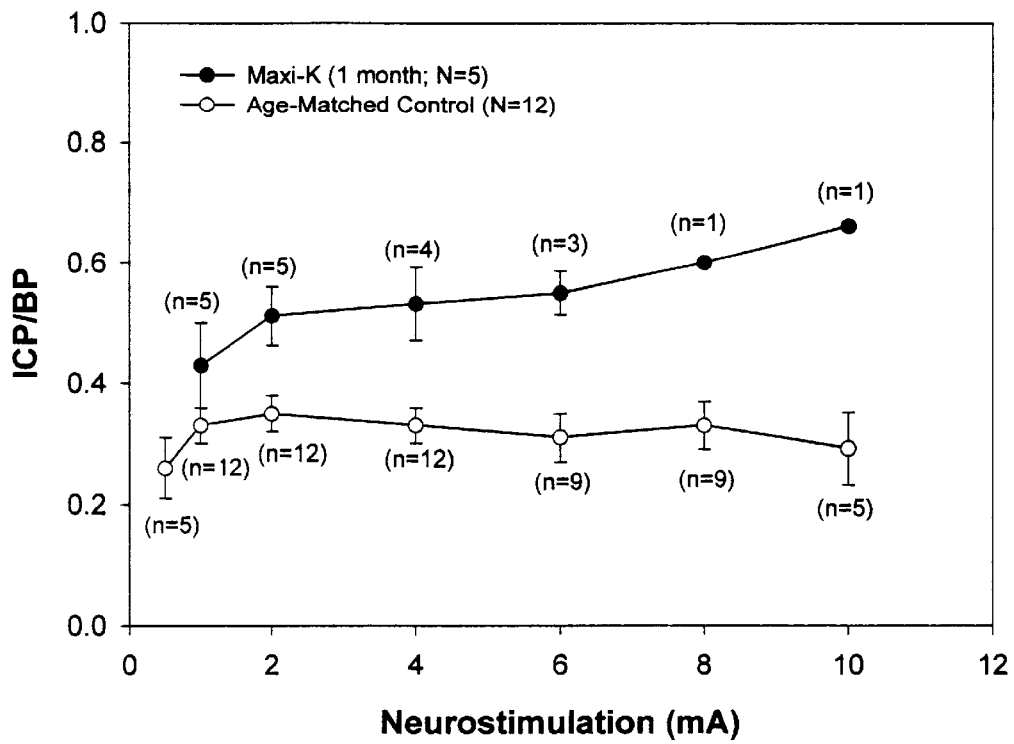
FIGS. 10A–10C show the mean value of the mean amplitude of the intracorporal pressure (ICP) responses of maxi-K-transfected animals (>9 months old at the time of injection), 1 month (FIG. 10A), 2 months (FIG. 10B), and 3–4 months (FIG. 10C) after a single intracavernous injection of pcDNA/hSlo naked DNA. For the purposes of statistical analysis, all of the age-matched control animals were considered to represent a single homogeneous population (see Experimental Details Section). The numbers (n) in parentheses refer to the total number of observations for each level of nerve stimulation. The numbers (N) given in the legends above the graphs refer to the total number of animals in each particular treatment group. The number of observations at each level of neurostimulation for the age-matched control animals is shown only in FIG. 10A, although it was the same for all panels. All data are presented as the mean values (±S.E.M.) of the mean amplitudes of the intracorporal pressure responses for each level of current stimulation. Two-Way analysis of variance revealed that there were significant differences in the mean amplitudes of the ICP responses at all levels of neurostimulation at the 1- and 2-month time points, post-injection. A similar trend was observed even at 3–4 months post-injection, although the small number of observations precluded statistical comparisons. ICP=intracorporal pressure; BP=mean blood pressure.
Figure 10B:
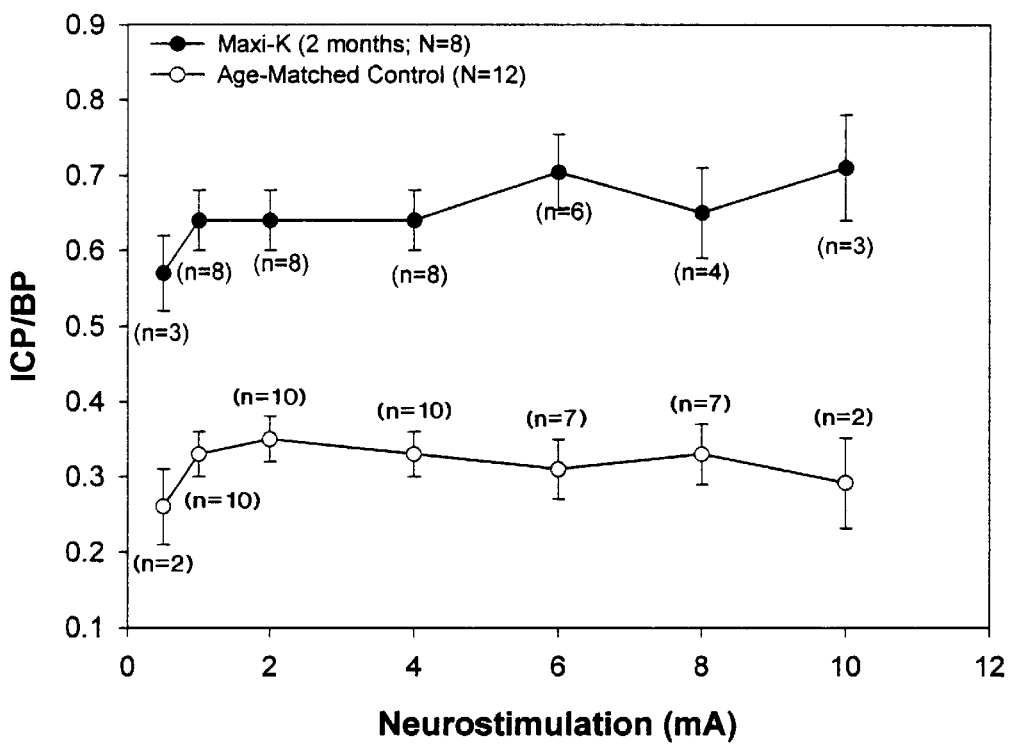
Figure 10C:
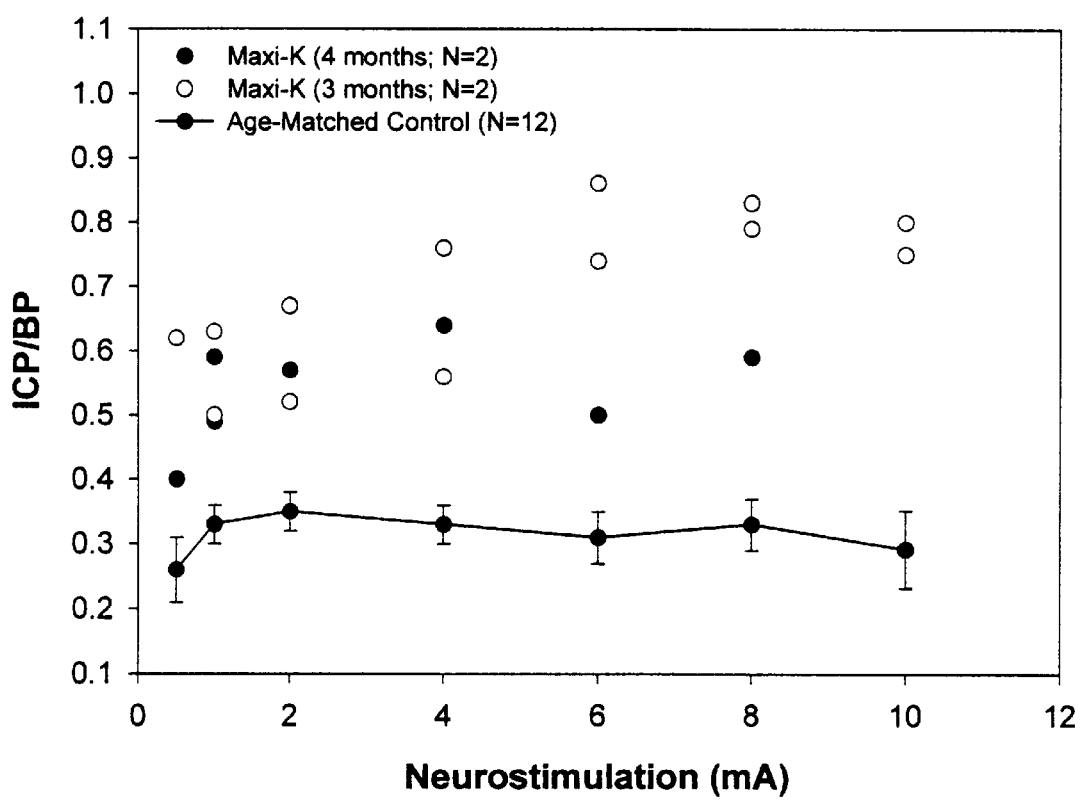

In addition, the pcDNA/hSlo-transfected animals were further subdivided based on whether the in vivo studies were conducted 1 month, 2 months, 3 months, or 4 months post-transfection, with age-matched control animals run in parallel. Consistent with the overall trend for the entire animal population (see FIG. 4), Two-Way analysis of variance revealed that intracorporal injection of the pcDNA/hSlo DNA was associated with significantly-elevated intracorporal pressures at all levels of current stimulation for both the 1-month (FIG. 10A) and 2-month (FIG. 10B) post-injection time points. Statistically-meaningful conclusions could not be drawn from the small number of observations at the 3-month and 4-month post-injection time points. However, FIG. 10C does suggest that qualitatively-similar results were obtained.

Figure 11A:
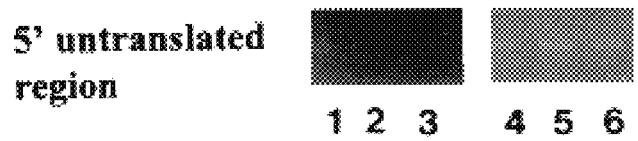
FIGS. 11A–11C set forth the results of an RT-PCR assay for gene expression in corporal tissue excised from recombinant human $K_{Ca}$ (hSlo)-transfected and control rats, 2 months after a single intracorporal microinjection of either pcDNA/$K_{Ca}$ or pcDNA alone (i.e., vector alone). Total RNA was then extracted from pcDNA/$K_{Ca}$-transfected tissues, as well as pcDNA-transfected control tissues, and was RT—PCR-amplified with primers, as described in the Experimental Details Section. As shown, amplification to the 5'-untranslated region resulted in a significant cDNA band from the pcDNA/$K_{Ca}$-transfected tissue (Lanes 4, 5, and 6 in FIG. 11A), but not from the pcDNA-transfected control tissue (Lanes 1, 2, and 3 in FIG. 11A). The full-length insert, with vector 5'- and 3'-untranslated sequences, was also RT—PCR-amplified from the pcDNA/$K_{Ca}$-transfected tissue (Lane 2 in FIG. 11C), but not from the pcDNA-transfected control (Lane 1 in FIG. 11C). The quality of the RNA from both groups of tissue was also examined with the primers that amplified the endogenous $K_{Ca}$. As indicated in FIG. 11B, the endogenous $K_{Ca}$ was amplified to a comparable level in the RNA from all tissues (pcDNA/$K_{Ca}$-transfected tissue: Lanes 4, 5, and 6; pcDNA control: Lanes 1, 2, and 3). The sequences for these primers are described in the Experimental Details Section. Note that each lane in FIGS. 11A and 11C corresponds to a corporal tissue sample obtained from a distinct animal (N=4). The samples depicted in Lanes 1–6 in FIG. 11B, though, were obtained from the same corporal tissues that are shown in FIG. 11A. Accordingly, these data were obtained from a total of four distinct hSlo-transfected rats, and four distinct vector-only rats, at the two-month time point.
Figure 11B:
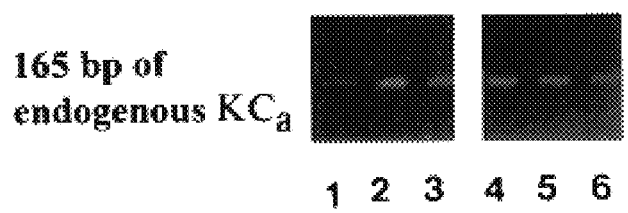
Figure 11C:
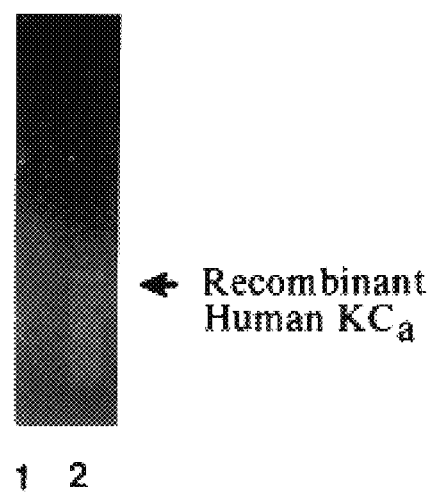
Figure 12:
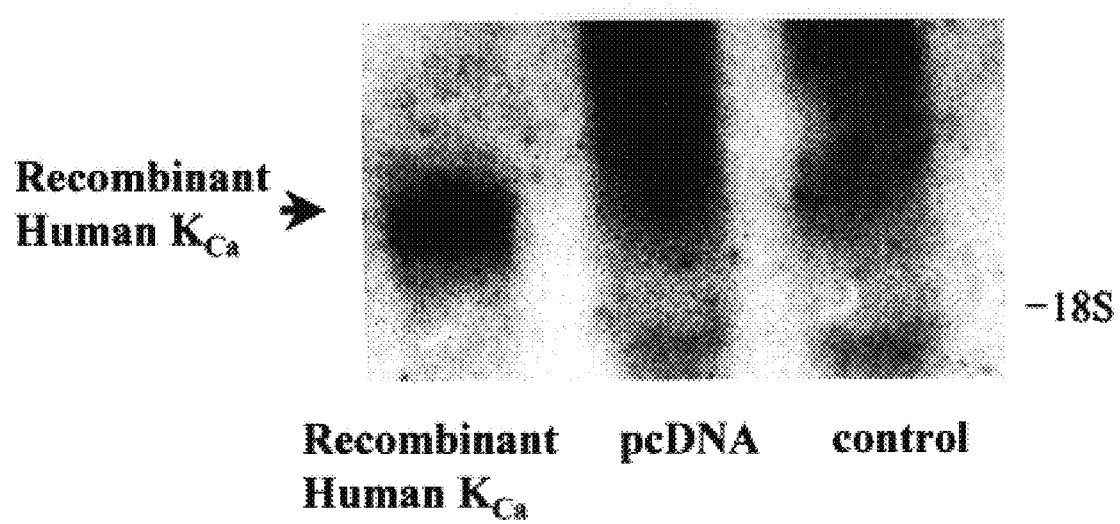
FIG. 12.
Figure 13:
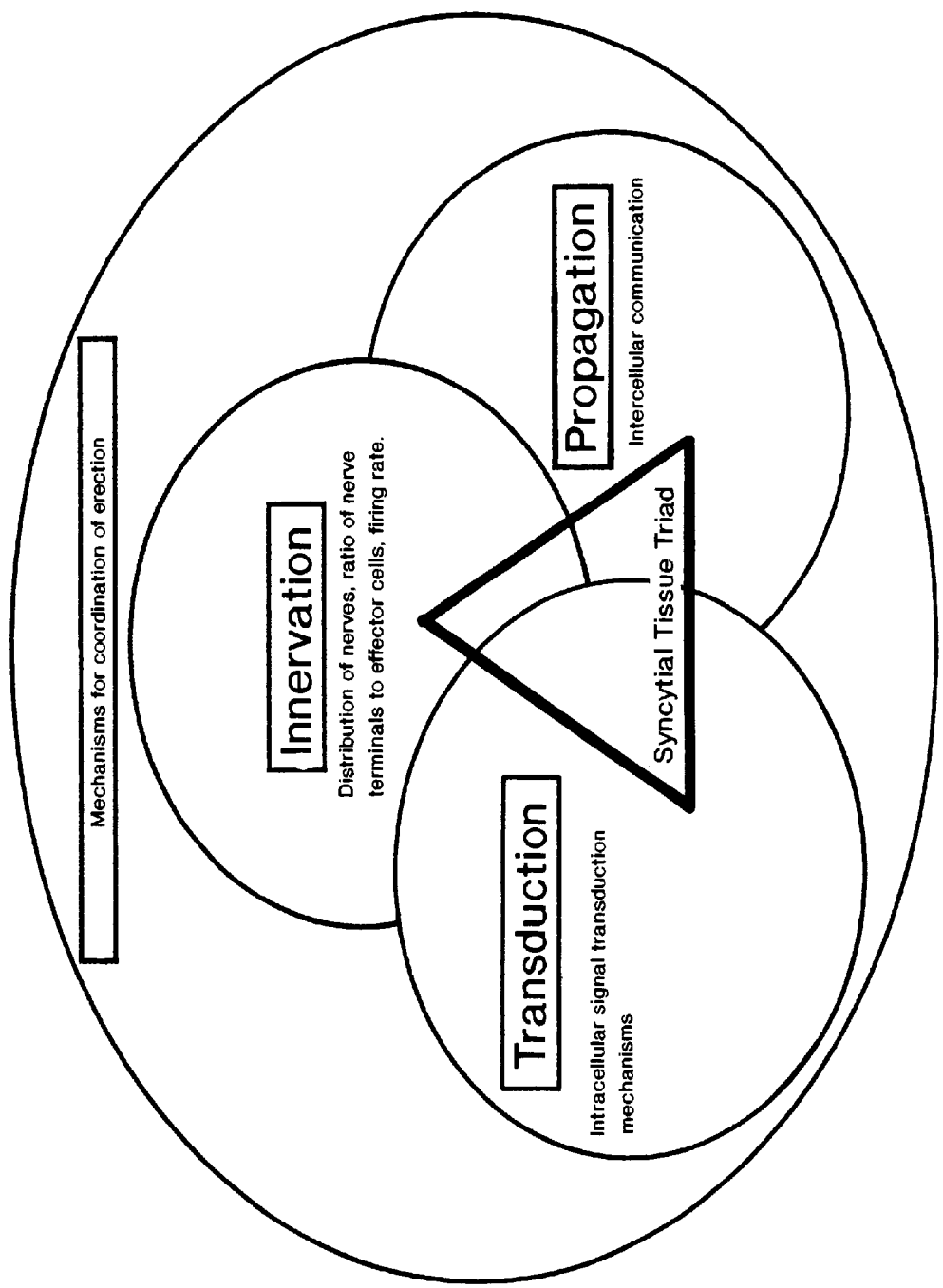
FIG. 13.
Figure 14A:
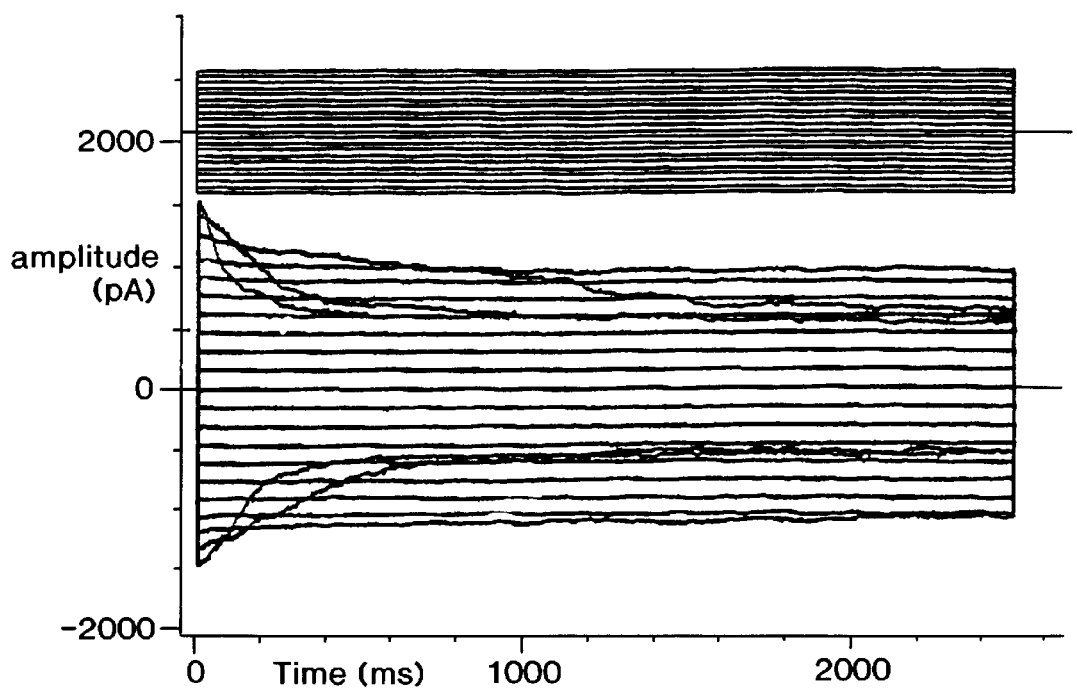
FIGS. 14A and 14B depict the voltage dependence of human bladder smooth muscle gap-junction channels.
Figure 14B:
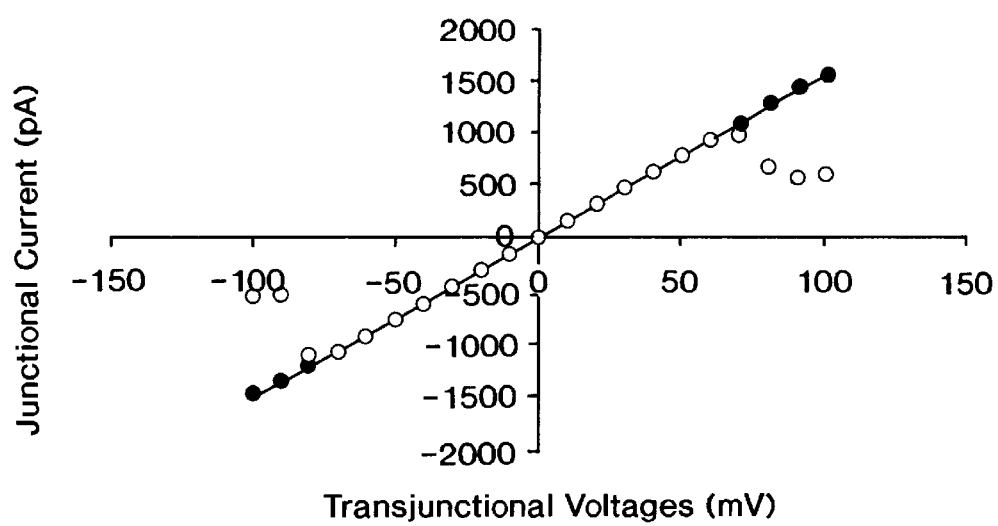
Figure 15:
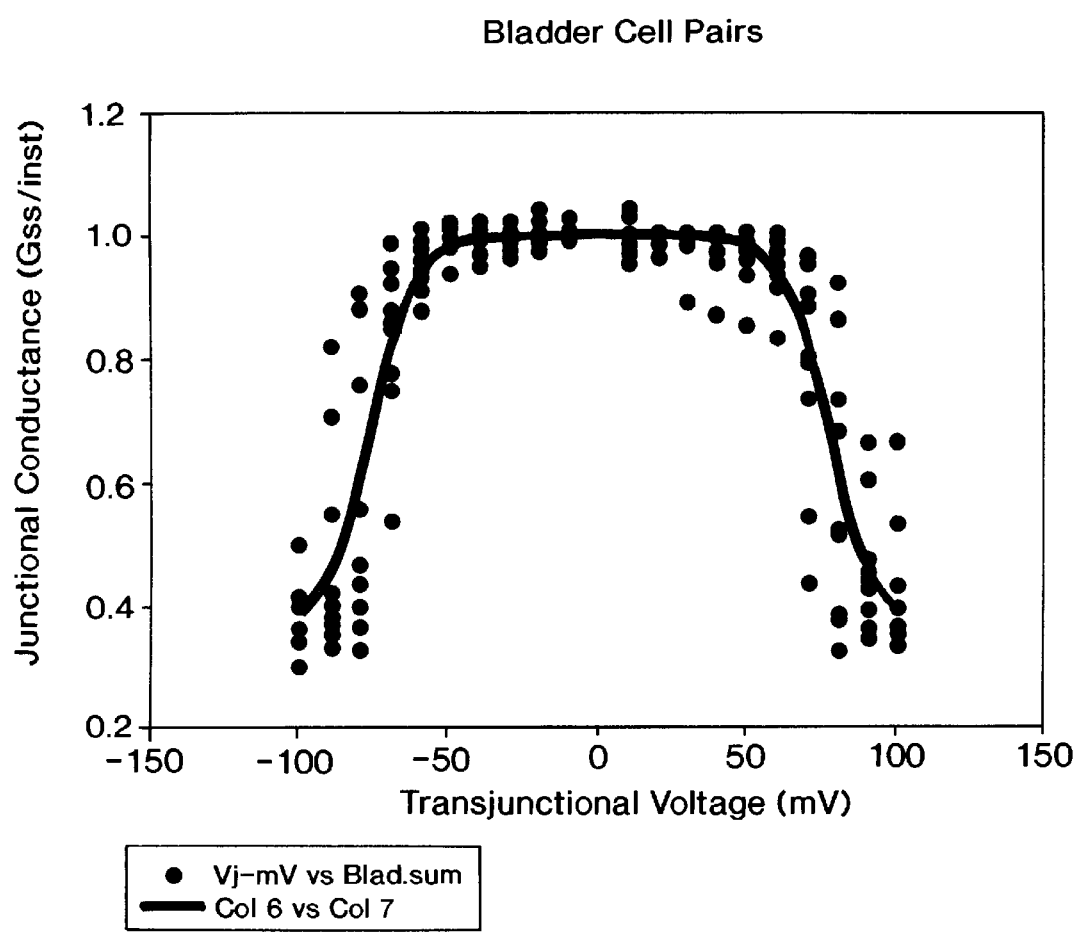
FIG. 15.
Figure 16A:
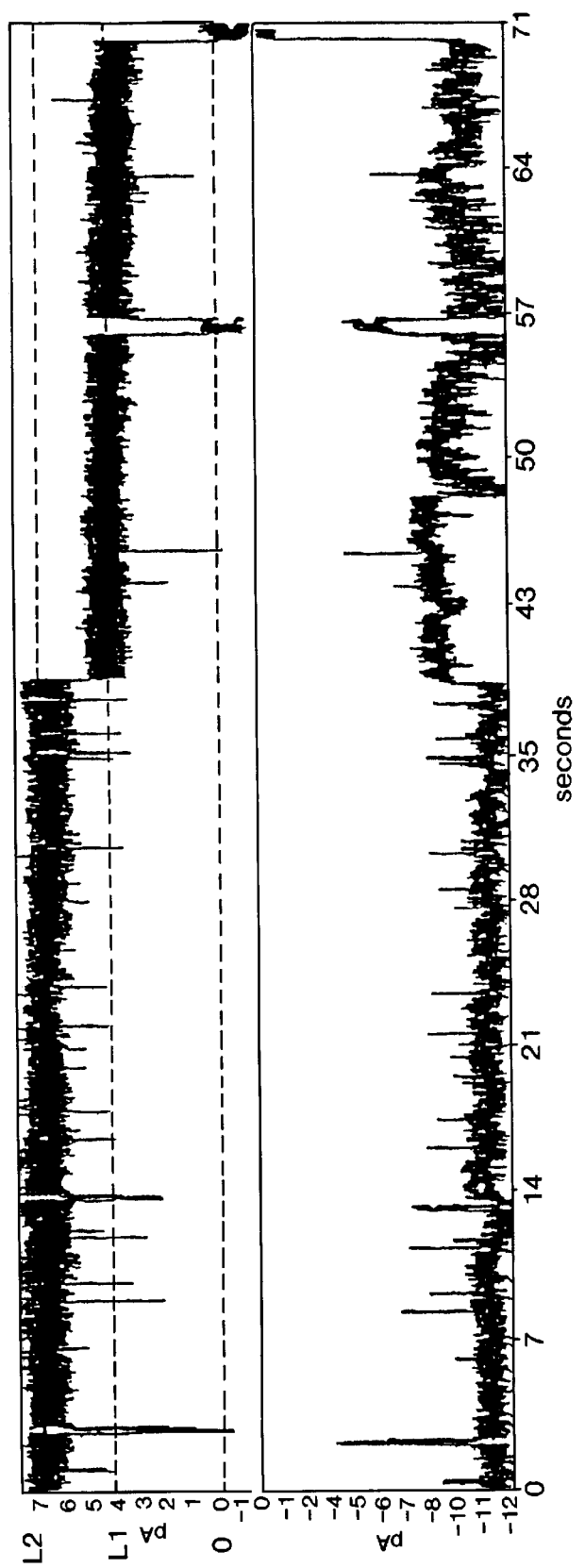
FIGS. 16A–16C illustrate the single gap-junction channel activity of a human bladder smooth muscle (HBSM) cell pair.
Figure 16B:
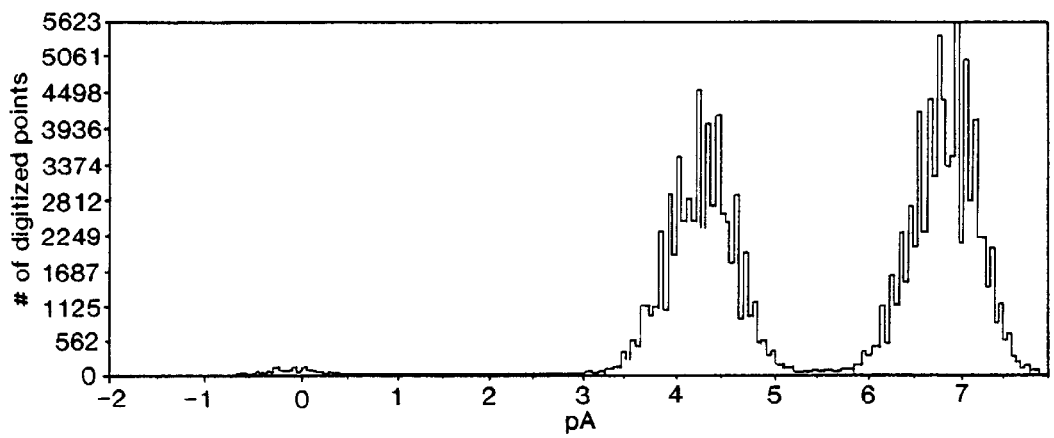
Figure 16C:
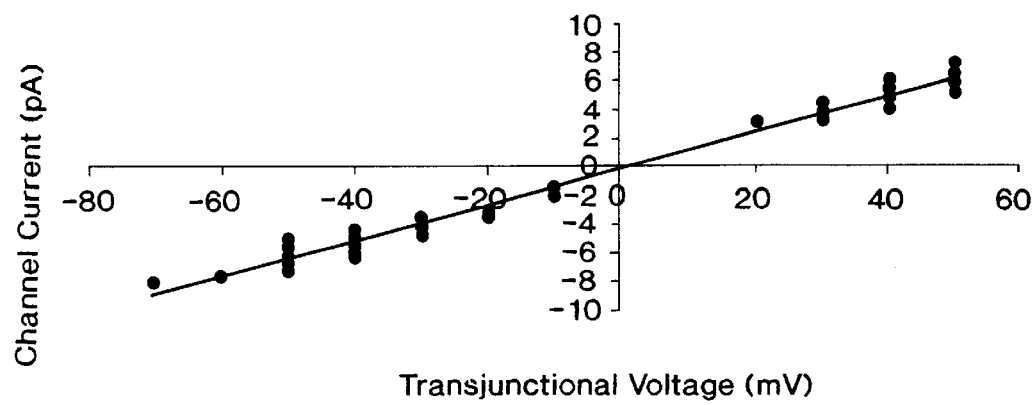
Figure 17A:
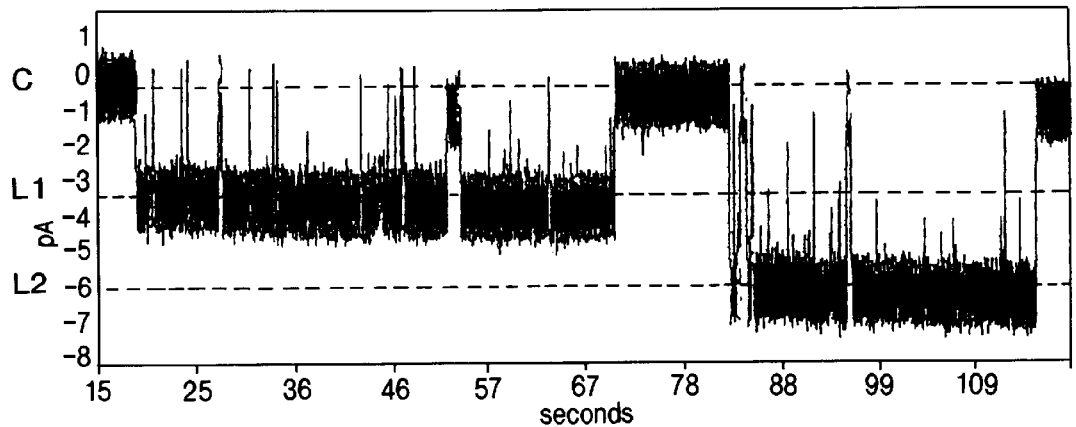
FIG. 17A shows a whole-cell current trace from a bladder smooth muscle cell pair during a ±40 mV $V_j$ step. Experiment and data-analysis procedures were similar to those presented in FIGS. 16A-16C. Three distinct conductance levels, and a closed state, were observed.
Figure 17B:
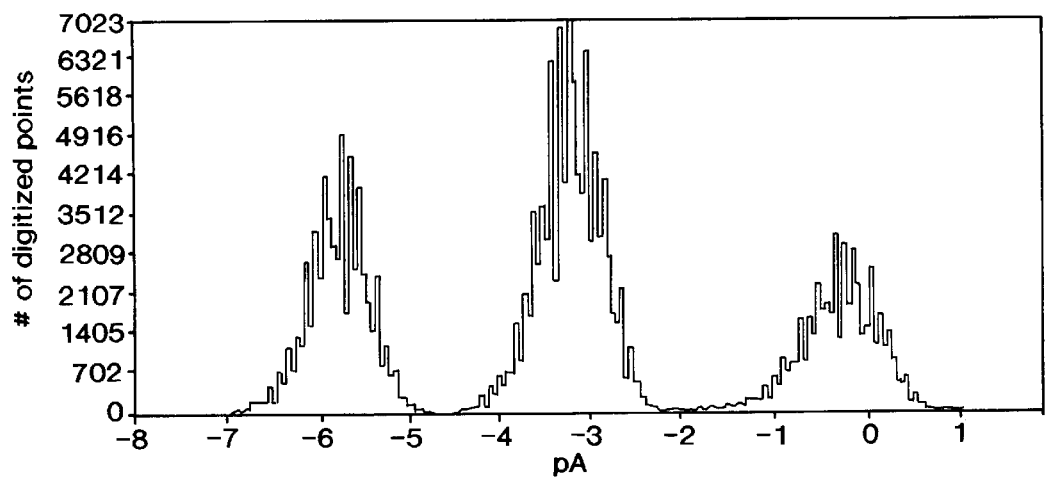
FIG. 17B shows an all-points amplitude histogram compiled from the entire 100-sec record (apart from the first 10 sec, which were omitted for being non-stationary). The measured single-channel conductances were 80 pS and 140 pS, respectively, and there were 65 total channel transitions. PO=open probability=0.45; MOT=mean open time=1.41 sec.
Figure 18A:
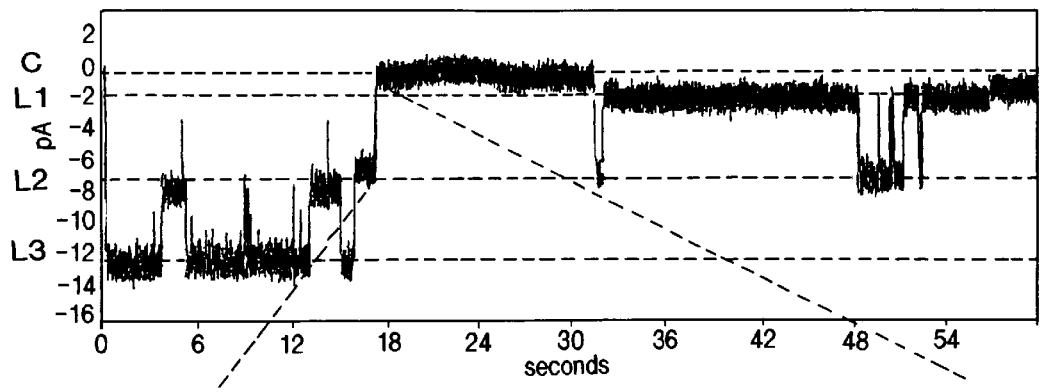
FIG. 18A depicts a whole-cell current trace from the third bladder smooth muscle cell pair under the experimental conditions described for FIGS. 16A–16C. Three distinct current levels (two fully open channels, and one residual state), as well as one closed state, were observed.
Figure 18B:
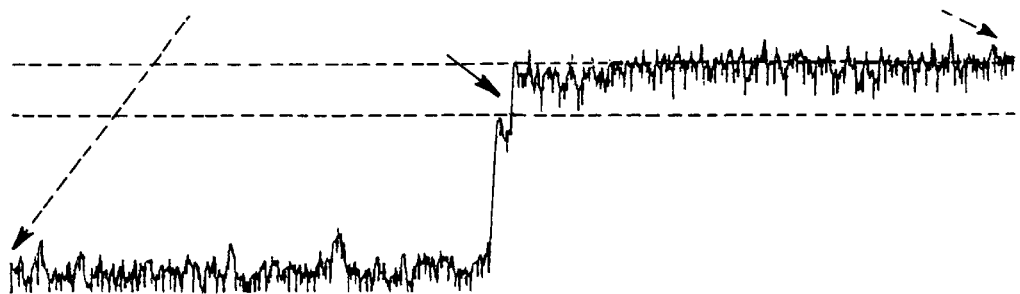
FIG. 18B shows a blow-out of the FIG. 18A segment indicated by the long arrow, and illustrates the transition between the main state, the residual state, and the closed state (indicated by a short arrow).
Figure 18C:
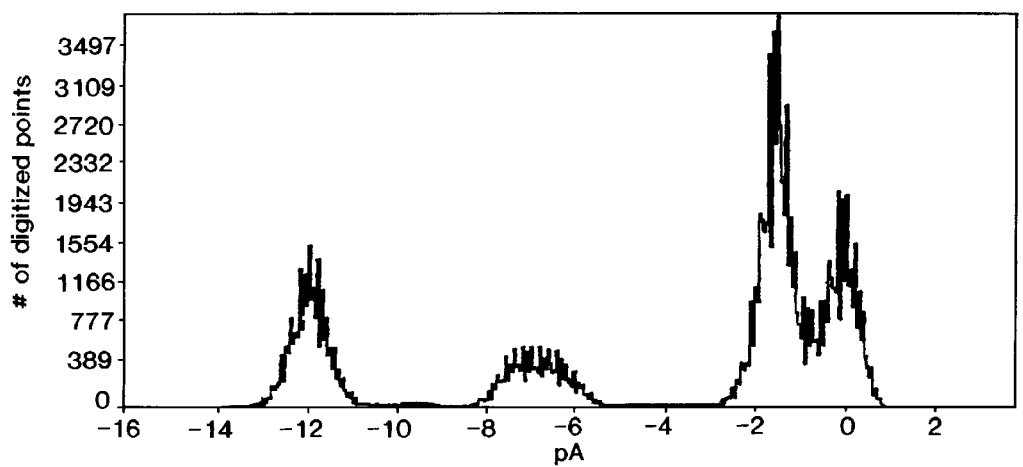
FIG. 18C depicts an all-points histogram compiled from the entire 60 sec shown in FIG. 18A. The three distinct current peaks give rise to channel conductances of 130 pS and 136 pS for the two fully-open channel states, and 36 pS for the residual state.

Incorporation of recombinant human $K_{Ca}$ (hSlo) into rat corporal smooth muscle. The gene expression level of recombinant human $K_{Ca}$ (hSlo) in transfected rat corporal smooth muscle was examined by both RT-PCR and Northern blot analyses. Total RNA from pcDNA/$K_{Ca}$-transfected tissue and pcDNA-transfected control tissue was RT-PCR-amplified with primers, as described in the Materials and Methods section, and as displayed in FIGS. 11A–11C. Amplification of the 5' untranslated region (FIG. 11A) resulted in a significant cDNA band from the pcDNA/$K_{Ca}$-transfected tissue (molecular size is approximately 4.2 kb), but not from the pcDNA-transfected control (FIG. 11C). The quality of the RNA from all tissues was further examined with primers that amplified the endogenous $K_{Ca}$. As indicated, the endogenous $K_{Ca}$ was amplified to a comparable level in all tissues (FIG. 11B). The presence of the recombinant human $K_{Ca}$ expression was further examined by Northern blotting with an hSlo insert as a probe (FIG. 12). Once again, RNA from the pcDNA/$K_{Ca}$-transfected tissue, but not from the pcDNA-transfected or control tissue, expressed a detectable level of recombinant human $K_{Ca}$. The recombinant human $K_{Ca}$ band was detected between the 18s and 28s RNA bands, with an approximate molecular size of 4.2 kb. In view of the high stringency conditions used in this assay (see Materials and Methods), it is not surprising that the endogenous $K_{Ca}$ was not detected.

b) Gene Transfer of $K_{ATP}$ Through a Single Intracavernous Injection

Figure 20:
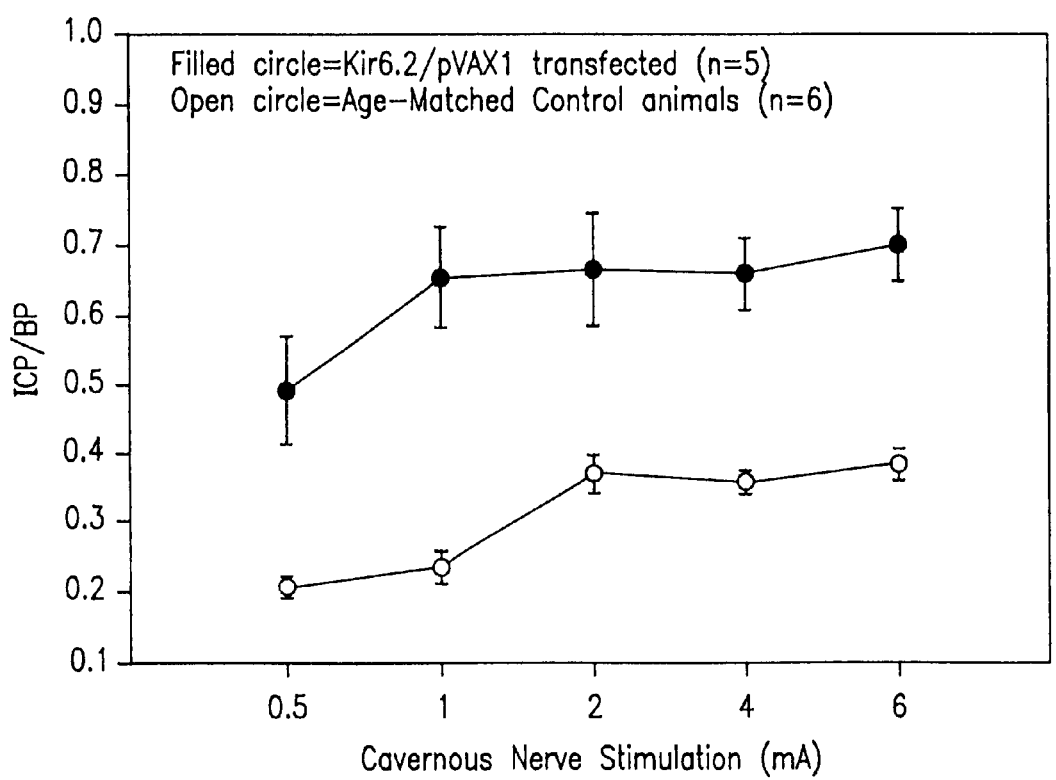
FIG. 20.

For these studies, retired breeders were injected with 100 μg of Kir6.2/pVAX1 (n=5) or phosphate-buffered saline (PBS) solution (age-matched control animals; n=6). Five days later, the nerve-stimulated intracorporal pressure (ICP) response was examined in all animals. As illustrated in FIG. 20, the animals that received the Kir6.2/pVAX1 injection had significantly greater cavernous-nerve-stimulated ICP responses than did age-matched control animals. These observations are remarkably similar to those made in relation to the experiments involving injection of a similar quantity of hSlo/pcDNA, and provide compelling evidence that Kir6.2 gene therapy may also be an attractive therapeutic option for the treatment of human erectile dysfunction.

Surprisingly, in contrast to the observations made in connection with hSlo, the Kir6.2 subunit is not known to form a functional channel by itself. In fact, while hSlo has been shown to form a functional channel in the absence of the β-subunit, the inventors are not aware of any demonstration that the Kir6.2 subunit (the pore-forming region of the $K_{ATP}$ channel) forms a functional channel in the absence of a corresponding SUR subunit. Presumably, the overexpressed recombinant Kir6.2 subunit, in vivo, combines with endogenous SUR(s) to form a functional channel.

II. Bladder Dysfunction Gene Therapy Experiments

For these experiments, 22 female Sprague-Dawley rats were subjected to partial urethral obstruction (PUO) for 6 weeks. Ten of these rats also received a single intravesical injection of naked pcDNA/hSlo cDNA (100 μg in 200 μl final volume) during ligature removal. Another 17 sham-operated rats were run in parallel. After 6 weeks, the urethral ligature was removed, and a catheter was inserted in the dome of the bladder, tunneled through the subcutaneous space, and exited between the shoulder blades. Two days later, rats were infused with saline for measurement of the micturition reflex (10 ml/hr - control; 20 ml/hr - PUO). In particular, the following parameters were measured: bladder capacity (BC), micturition volume (MV), residual volume (RV), threshold pressure (TP), micturition pressure (MP), and basal pressure (BP).

Figure 21A:
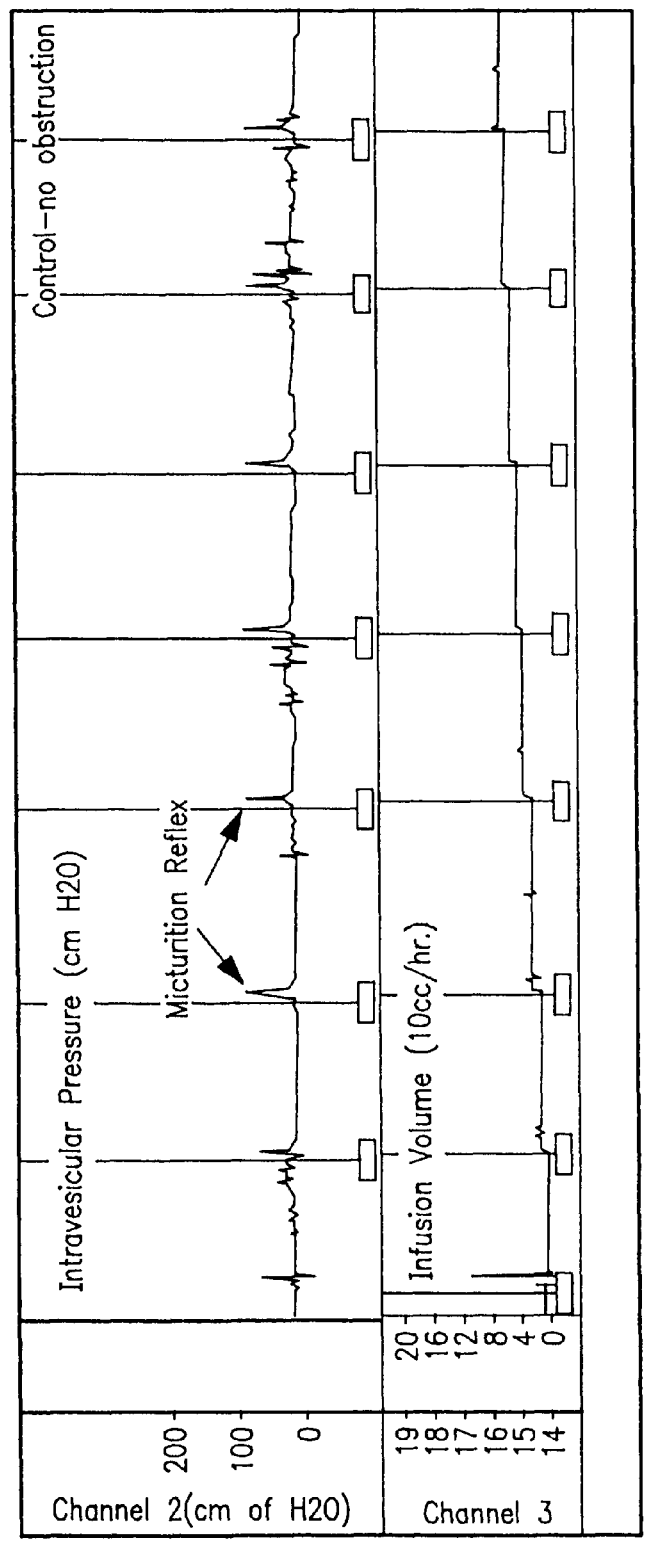
Figure 2I:
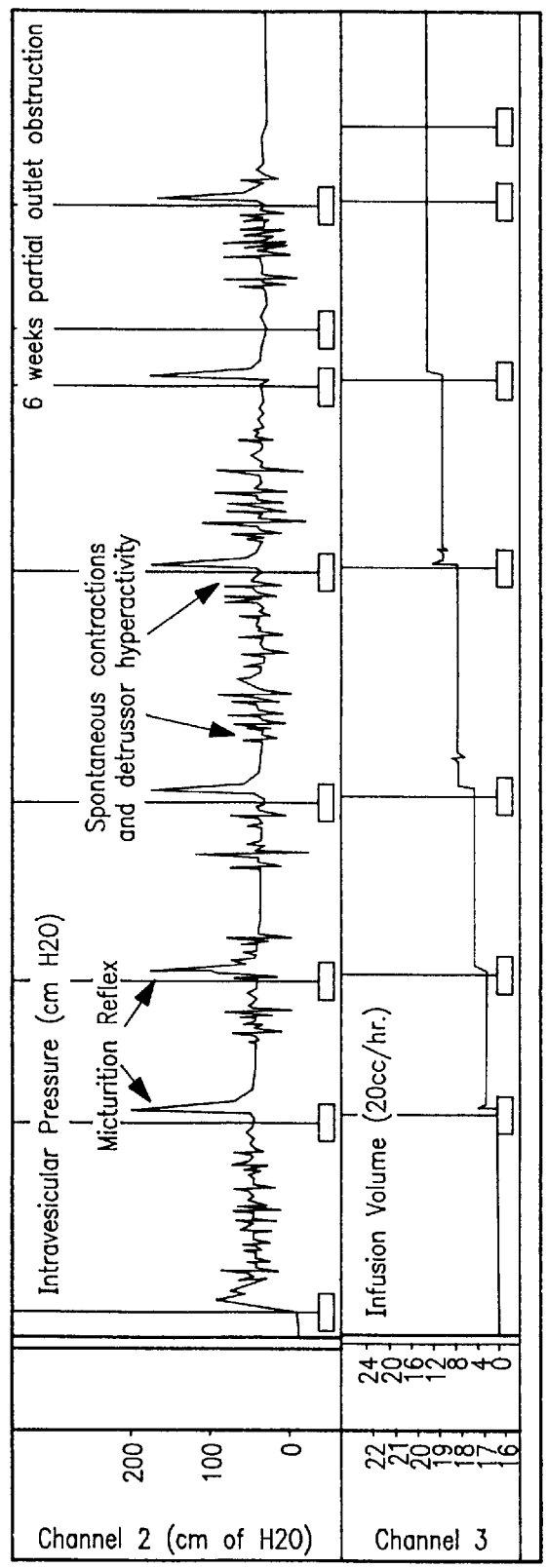

According to the results of these experiments, 6 weeks of PUO were associated with the presence of bladder hyperactivity (contractions between micturitions), as well as significant increases in all parameters measured, except for BP. Importantly, as illustrated in Table 7 and FIG. 21, the maxi-K-treated animals, relative to the untreated PUO rats, exhibited a nearly-complete ablation of hyperactivity in the absence of any detectable effect on other parameters of bladder function. Thus, this study documents the important role of $K_{Ca}$-mediated hyperpolarizing currents in modulating bladder myocyte function, and indicates that gene therapy may be an effective therapeutic modality for the treatment of urinary incontinence (i.e., bladder hyperactivity).

TABLE 7

Micturition reflex parameters in age-matched control and six-week-obstructed rats

| | WT (mg) | MP | THP | BP | BC | MV | RV | IP (MIP-BP) |
|---|---|---|---|---|---|---|---|---|
| Control: unobstructed (n = 17) | 171 ± 15.0 | 73.9 ± 4.99 | 22.3 ± 2.1 | 12.6 ± 1.09 | 1.2 ± 0.1 | 1.13 ± 0.10 | 1.13 ± 0.04 | 3.49 ± 0.79 |
| [a]Obstructed: hSlo-injected (n = 12) | *547.6 ± 55.4 | *128.9 ± 16.1 | *36.3 ± 4.30 | *22.1 ± 43.9 | *3.44 ± 0.41 | *3.22 ± 0.39 | *,**0.33 ± 0.10 | **5.59 1.05 |
| Obstructed: untreated (n = 10) | *473.1 ± 56.6 | *132.7 ± 17.9 | *39.3 ± 3.6 | *18.8 ± 1.9 | *2.91 ± 0.62 | *2.94 ± 0.65 | 0.09 ± 0.05 | 9.37 ± 1.79 |

[a]100 μg hSlo/pcDNA in 200 μl PBS
Control: sham-operated, unobstructed, age-matched control animals; WT: bladder weight (mg); MP: micturition pressure; THP: threshold pressure; BP: basal pressure; BC: bladder capacity; MV: micturition volume; RV: residual volume; IP: intermicturition pressure (the mean pressure over the entire intermicturition interval minus the basal pressure on the same animal)
*significantly different from sham-operated; p < 0.05
**significantly different from control (obstructed but not treated); p < 0.05, One-Way ANOVA, with Newman Keuls post-hoc pairwise comparisions C. Conclusion Many recent advances have been made in the application of gene therapy to the treatment of human diseases. In particular, techniques for gene transfer into vascular smooth muscle cells have been developed in an effort to provide a novel therapeutic strategy for the treatment of several cardiovascular diseases, including atherosclerosis, vasculitis, and restenosis after balloon angioplasty. Such studies have provided important information on the efficiency and persistence of gene-transfer methods in smooth muscle cells.

In light of these seminal observations, the initial and explicit aim of these studies was to begin to evaluate the feasibility of somatic gene transfer into corporal smooth muscle as a novel therapeutic strategy for the treatment of erectile dysfunction. The rationale for this approach was related to the fact that the tone of corporal smooth muscle in the specialized vascular tissue of the penis plays a critical role in modulating the flow of blood to and from the penis, thereby determining erectile capacity. In view of this role, corporal smooth muscle cells are a logical target for molecular intervention in the treatment of erectile dysfunction. Given the central role of the maxi-K channel in modulating human corporal smooth muscle tone, the inventors examined the physiological impact of transfection of penile and bladder smooth muscle with hSlo cDNA in a rat model in vivo. The effects of $K_{ATP}$ on penile smooth muscle were also examined. The major findings are summarized as follows.

Figure 7B:

Firstly, after a single intracorporal injection of naked pCMVβ/LacZ DNA (see Materials and Methods), expression of β-galactosidase activity was sustained for at least 75 days. This clearly demonstrated that, in the rat corpora in vivo, it is feasible to achieve relatively prolonged expression of extrachromosomal genes that encode physiologically-detectable protein products (see FIGS. 7A and 7B). Consistent with these observations, the mean amplitude of the nerve-stimulated ICP response was significantly augmented over a similar time course in rats in vivo, following a single intracavernous injection of naked pcDNA/hSlo DNA (see FIGS. 8–10C). Moreover, both RT-PCR techniques and Northern blots revealed that, at least for the two-month time point, the observed augmentation in the nerve-stimulated ICP response was correlated with increased expression of the hSlo mRNA (FIGS. 11A–12). Presumably, the same holds true for the longer time points (i.e., 3–4 months), although this was not directly evaluated in this series of experiments. There was no detectable effect of either vector alone or sham surgery (see Materials and Methods) on the nerve-stimulated ICP responses at any time point examined in these initial studies (see FIGS. 8–10C). Taken together, these data provide compelling evidence that the enhancement in the nerve-stimulated ICP responses observed in the maxi-K-transfected animals, relative to the age-matched control animals, is most certainly related to the extrachromosomal expression of the hSlo cDNA, and a nominally-corresponding increase in expression of the maxi-K channel protein.

In order to better judge the physiological meaning of the increase in ICP in the maxi-K-transfected animals, a second group of young control (2- or 3-month-old) animals was also studied. As illustrated in FIG. 8, the increase in the mean amplitude of the nerve-stimulated ICP/BP ratio in the 10–13-month-old, maxi-K-transfected animals approximated, but did not exceed, the response observed in the adolescent rats. This would suggest that the putative increased expression of the maxi-K channel in the "older" animals was associated with a nerve-stimulated ICP response that was nominally equivalent to the best response expected under "normal" physiological conditions in younger animals.

With respect to the mechanistic basis for the inventors' observations, it is clear that the injected hSlo cDNA was likely taken up into all cell types present in the rat corpora. In this regard, it cannot be unequivocally stated that the uptake of hSlo cDNA in the endothelial cells plays a role in mediating the observed increases in nerve-stimulated ICP. Nevertheless, the present discussion is confined to putative effects resulting from uptake and expression in corporal smooth muscle cells. This seems reasonable in view of the fact that corporal smooth muscle cells make up the vast majority of the corporal parenchyma; moreover, in the penis, relaxation of the corporal smooth muscle is both necessary and sufficient for erection. A more precise analysis of the cellular disposition of the hSlo cDNA, the resulting expression of the α-subunit of the maxi-K channel, and the relative percentage of cells thus affected, will necessarily be the province of future investigations.

While a cause-effect relationship was not established in the present investigation, it can be presumed that the mechanistic basis for the increased maxi-K channel activity would be related to the commensurate augmentation in the hyperpolarizing ability of the corporal smooth muscle cells. Moreover, given the exquisite dependence of sustained corporal smooth-muscle contraction on continuous transmembrane $Ca^{2+}$ flux, it is reasonable to suggest that the increase in hyperpolarization is associated with a decreased transmembrane $Ca^{2+}$ flux through L-type voltage-dependent $Ca^{2+}$ channels, with a corresponding decrease in the free intracellular $Ca^{2+}$ concentration, so as to ultimately promote greater corporal smooth-muscle relaxation. Accordingly, an increase in the expression of the maxi-K channel would logically suggest a resultant increase in the sensitivity of the smooth muscle cells, up to the same level of neural stimulation.

As with all other in vivo gene-therapy approaches, the potential utility of the present genetic technique in treating human erectile dysfunction and bladder dysfunction depends on two considerations: (1) the likelihood of affecting only the desired cell type(s); and (2) the percentage of target cells which must be affected in order to see a physiologically-relevant therapeutic effect. In light of such considerations, there are two main reasons for suspecting that gene therapy for erectile or bladder dysfunction may be inherently more successful than its proposed uses in other, more systemic, cardiovascular disorders, such as atherosclerosis, vasculitis, and restenosis after balloon angioplasty.

Firstly, it is a well-documented fact that corporal smooth muscle cells, as well as bladder smooth muscle cells, are interconnected by a ubiquitously-distributed population of intercellular channels known as gap junction proteins, with connexin 43 as the predominant isoform expressed in the human penis and bladder. These intercellular channels provide partial cytoplasmic continuity between adjacent smooth muscle cells, allowing the intercellular exchange of physiologically-relevant ions ($K^+$ and $Ca^{2+}$) and second-messenger molecules ($IP_3$, cAMP, and cGMP). As such, the presence of gap junctions in the rat and human provides an important anatomic substrate for coordinating the syncytial contraction and relaxation responses that are a prerequisite to normal penile erection and detumescence, and normal bladder function. In particular, intercellular communication among the smooth muscle cells permits cells that are not directly activated by a relevant neuronal/hormonal signal to be rapidly, albeit indirectly, recruited into the contraction or relaxation response.

To summarize, gap junctions are implicated in the gene therapy of erectile and bladder dysfunction because their presence ensures that only a fraction of the smooth muscle cells need to be genetically modified in order to effect rather global changes in smooth muscle tone. This is crucially important because it minimizes the need to use more aggressive gene-incorporation strategies (e.g., adenoviral or retroviral incorporation) which have a concomitantly greater number of side effects and concerns (e.g., insertional mutagenesis or immunological reactions).

Secondly, the method of gene therapy proposed herein is designed to take advantage of the fact that relatively subtle alterations in the balance between contracting and relaxing stimuli can result in profound alterations in erectile or bladder physiology and function. The goal of gene therapy is, therefore, to restore a more normal balance between contracting and relaxing stimuli following expression of (an) exogenous gene(s) that code(s) for physiologically-relevant proteins in smooth muscle (e.g., the maxi-K channel or $K_{ATP}$). In light of the multifactorial nature of erectile and bladder dysfunctions in humans, there may, in fact, be many distinct genetic therapy strategies that will be effective in the restoration of erectile potency. For example, it is worth noting that qualitatively similar effects on ICP were observed following the intracavernous injection of an inducible form of NOS in the rat model. Thus, if expression of these or other extrachromosomal genes can be maintained in humans for a period of weeks to months (as the preliminary data herein indicates), it is conceivable that a patient could obtain "normal" erections, or "normal" bladder function, in the absence of any other exogenous manipulation, during this time period. Clearly, this would be a major advance over all other currently-available therapies.

Taken together, the foregoing data are consistent with the supposition that increased maxi-K channel activity, following a single intracorporal injection of naked hSlo DNA, results from the presence of a greater number of maxi-K channels in some fraction of corporal smooth muscle cells. In turn, this results in a greater hyperpolarization for any given level of neural stimulus, presumably altering intracellular calcium mobilization/homeostasis, and thereby promoting greater corporal smooth-muscle relaxation. In conclusion, it seems reasonable to assume that the relatively-stable transfection of smooth muscle cells with the human smooth muscle maxi-K channel cDNA represents an important and physiologically-relevant strategy for the novel molecular manipulation of smooth muscle tone in the treatment of organic erectile dysfunction and bladder dysfunction.

What is claimed is:

1. A method for treating penile flaccidity caused by heightened contractility of penile smooth muscle in a subject, comprising introducing directly into penile smooth muscle cells of the subject a DNA sequence comprising a promoter sequence operably linked to a sequence encoding a $K_{ATP}$ channel subunit protein, wherein the channel subunit protein is Kir6.2, and wherein said Kir6.2 is expressed in said penile smooth muscle cells such that penile smooth muscle tone is regulated, and wherein the regulation of penile smooth muscle tone results in less heightened contractility of penile smooth muscle in said subject.

2. The method of claim 1, wherein the DNA sequence is introduced by naked DNA transfer.

* * * * *